(12) United States Patent
Chandrasekharappa et al.

(10) Patent No.: US 7,358,347 B1
(45) Date of Patent: Apr. 15, 2008

(54) MEN1, THE GENE ASSOCIATED WITH MULTIPLE ENDOCRINE NEOPLASIA TYPE 1, MENIN POLYPEPTIDES AND USES THEREOF

(75) Inventors: Settara Chandrasekharappa, Gaithersburg, MD (US); Siradanahalli Guru, Bethesda, MD (US); Pachiappan Manickam, Huntsville, AL (US); Francis S. Collins, Rockville, MD (US); Michael R. Emmert-Buck, Silver Spring, MD (US); Larisa V. Debelenko, New York, NY (US); Irina A. Lubensky, Silver Spring, MD (US); Lance A. Liotta, Bethesda, MD (US); Sunita K. Agarwal, Gaithersburg, MD (US); Allen M. Spiegel, Bethesda, MD (US); A. Lee Burns, Rockville, MD (US); Stephen J. Marx, Chevy Chase, MD (US); Zhengping Zhuang, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/380,337

(22) PCT Filed: Mar. 4, 1998

(86) PCT No.: PCT/US98/04258

§ 371 (c)(1),
(2), (4) Date: Mar. 6, 2000

(87) PCT Pub. No.: WO98/39439

PCT Pub. Date: Sep. 11, 1998

Related U.S. Application Data

(60) Provisional application No. 60/040,269, filed on Mar. 5, 1997.

(51) Int. Cl.
C07H 21/00 (2006.01)
C07H 21/02 (2006.01)
C07H 21/04 (2006.01)
C12Q 1/68 (2006.01)
C12P 19/26 (2006.01)
C12P 19/34 (2006.01)

(52) U.S. Cl. .................. 536/23.1; 536/23.5; 536/24.3; 536/24.31; 536/24.33; 536/25.3; 435/6; 435/84; 435/91.1; 435/91.2

(58) Field of Classification Search ............... 536/23.1, 536/23.5, 24.3, 24.33; 435/320.1, 69.1, 7.1, 435/7.23
See application file for complete search history.

(56) References Cited

U.S. PATENT DOCUMENTS

| 4,594,318 | A | * | 6/1986 | Gusella et al. ................. 435/6 |
| 5,559,023 | A | * | 9/1996 | Nakamura et al. ........ 435/240.2 |
| 5,736,330 | A | * | 4/1998 | Fulton ............................ 435/6 |
| 6,107,462 | A | * | 8/2000 | Rine et al. |

OTHER PUBLICATIONS

Thankker et al., Seronon Symp. Publ., Hereditary Tumors, pp. 77-88, 1991.*

(Continued)

*Primary Examiner*—Susan Ungar
(74) *Attorney, Agent, or Firm*—Townsend and Townsend and Crew LLP

(57) ABSTRACT

The invention relates to the discovery of a novel tumor suppressor gene which is associated with multiple endocrine neoplasia type 1. The gene has been designated MEN1 and the gene product is menin. The absence of this protein and associated mutations in the corresponding gene have been identified in individuals suffering from multiple endocrine neoplasia type 1. The identification of this marker for multiple endocrine neoplasia type 1 has diagnostic uses as well as for gene therapy.

17 Claims, 4 Drawing Sheets

OTHER PUBLICATIONS

Bystrom et al., PNAS vol. 87, pp. 1968-1972, Mar. 1990.*
Sambrook et al., Molecular Cloning, chapter 14, 1989.*
Bork, Genome Research, vol. 10, pp. 398-400, 2000.*
Lazar et al., Molecular and Cellular Biology, vol. 8, No. 3, pp. 1247-1252, Mar. 1988.*
Bowie et al., Science, vol. 247, pp. 1306-1310, Mar. 1990.*
Burgess et al., The Journal of Cell Biology, vol. 111, pp. 2129-2138, Nov. 1990.*
Sambrook et al., Molecular Cloning, chapter 16, 1989.*
Roitt et al (Immunology, 1993, Mosby, St. Louis, p. 6.4-6.5).*
Alberts et al (Molecular Biology of the Cell, 3rd edition, 1994, p. 465).*
Shantz and Pegg (Int J. Biochem Cell Bio., 1999, 31:107-122).*
McClean and Hill (Eur. J. Can., 1993, 29A:2243-2248).*
Fu et al (EMBO J., 1996, 15:4392-4401).*
Orkin et al (Report and Recommendations of the Panel to Assess the NIH Investment in Research on GEne Therapy, 19950.*
Marchall (Science, 1995, 269:1050-1055).*
Culver et al (TIG, 1994, 10:174-178).*
Hodgson (Exp. Opin. Ther. Patents, 1995, 5:459-468).*
Miller et al (FASEB J., 1995, 9:190-199).*
Nature Biotechnology, 1997, 15:815).*
Agarwal et al (Human Molecular Genetics, 1997, 6:1169-1175).*
Wautot (Human Mutation, 2002, 20:35-47).*
Chandrasekharappa et al., "Positional cloning of the gene for multiple endocrine neoplasia-type 1," *Science* (1997) 276: 404-407.
Kedra et al., "The germinal center kinase gene and a novel CDC25-like gene are located in the vicinity of the PYGM gene on 11q13," *Hum. Genet.* (1997) 100:611-619.
Larsson et al., "Multiple endocrine neoplasia type 1 gene maps to chromosomeII and it lost in insulinoma," *Nature* (1988) 332: 85-87.

* cited by examiner

Mutations in the MEN1 gene

| Exon | Mutation | Nature of Mutation |
|---|---|---|
| Exon 2 from ATG | P12L (CCG/CTG) | Missense |
| | L22R (CTG/CGG) | Missense |
| | 313delC | Frameshift |
| | 357del4 | Frameshift |
| | 416delC | Frameshift |
| | K119del | In-frame deletion |
| | K120X (AAG/TAG) | Nonsense |
| | 512delC | Frameshift |
| | H139D (CAC/GAC) | Missense |
| | H139Y (CAC/CAT) | Missense |
| | F144V (TTC/GTC) | Missense |
| | E26K (GAG->AAG) | Missense |
| | R108X(CGA->TGA)* | Nonsense |
| | 134del13 | Frameshift |
| | 358del4 | Frameshift |
| | 358del25 | Frameshift |
| | I86F(ATC->TTC) | Missense |
| | 483delAT | Frameshift |
| | W126G(TGG->GGG) | Missense |
| | 545insT | Frameshift |
| Exon 3 | A160P (GCT/CCT) | Missense |
| | A176P (GCC/CCC) | Missense |
| | W183X (TGG/TAG) | Nonsense |
| | W198X (TGG/TGA) | Nonsense |
| | 713delG | Frameshift |
| | 735del4 | Frameshift |
| | 764+3 (A->G) | Frameshift |
| | F159C(TTT->TGT) | Missense |
| Exon 4 | A242V (GCC/GTC) | Missense |
| | Q260X (CAG/TAG) | Nonsense |
| | 875insA | Frameshift |
| Exon 5 | W265X (TGG/TAG) | Nonsense |
| | 934+1 (G->A) | Frameshift |
| Exon 6 | L286P (CTA/CCA) | Missense |
| Exon 7 | S308X (TCA/TAA) | Nonsense |
| | A309P (GCC/CCC) | Missense |
| | Y312X (TAC/TAA) | Nonsense |
| | Y323X (TAC/TAG) | Nonsense |
| | 1132delG | Frameshift |
| | T344R (ACG/AGG) | Missense |
| Exon 8 | E363del | In-frame deletion |
| | 1202del2 | Frameshift |
| | 1260delG | Frameshift |
| | 1279ins11 | Frameshift |
| | 1212del? | Frameshift |
| Exon 9 | D418del* | In-frame deletion |
| | W436R (TGG/CGG) | Missense |
| | W436X (TGG/TAG) | Nonsense |
| | F447S(TTT/TCT) | Missense |
| | D418N(GAC->AAC) | Missense |
| | F410L (TTC->TTA) | Missense |
| Exon 10 to stop | R460X (CGA/TGA) | Nonsense |
| | 1484del6 | Frameshift |
| | 1509insGA | Frameshift |
| | 1650delC | Frameshift |
| | 1650insC | Frameshift |
| | R527X (CGA/TGA) | Nonsense |
| | M561T (ATG->ACG) | Missense |
| | 1812del5 | Frameshift |
| | 1702G->C | Frameshift |
| | 1699delA | Frameshift |
| | 1461delG | Frameshift |
| | K502M (AAG->ATG) | Missense |
| | A535V (GCT->GTT) | Missense |
| | S543L(TCA->TTA) | Missense |

MEN1, THE GENE ASSOCIATED WITH MULTIPLE ENDOCRINE NEOPLASIA TYPE 1, MENIN POLYPEPTIDES AND USES THEREOF

CROSS-REFERENCE TO RELATED APPLICATION

This application claims priority to U.S. Provisional Patent Application Ser. No. 60/040,269, filed Mar. 5, 1997 now abandoned.

FIELD OF THE INVENTION

This invention relates to the discovery of a novel tumor suppressor gene which is associated with multiple endocrine neoplasia type 1. The gene has been designated MEN1 and the gene product is menin. The lack of a functional menin polypeptide, either by absence of the protein, its alteration and/or associated mutations in the corresponding gene, have been identified in individuals with familial multiple endocrine neoplasia type 1 (FMEN1) and suffering from multiple endocrine neoplasia type 1. The identification of MEN1 as a marker for multiple endocrine neoplasia type 1 has diagnostic uses in cancer and in endocrine disease, as well as application for gene therapy.

BACKGROUND OF THE INVENTION

Familial multiple endocrine neoplasia type 1 (FMEN1) is an autosomal dominant familial cancer syndrome characterized by the frequent occurrence of tumors in the parathyroids, gastro-intestinal endocrine tissues (e.g., gastrinomas, tumors of the endocrine duodenum), enteropancreatic endocrine tissues, the anterior pituitary, and occasionally other sites. In keeping with the hypothesis originally articulated by Knudson for retinoblastoma (see Knudson (1971) *Proc. Natl. Acad. Sci. U.S.A.* 68:820), most of the genes responsible for familial cancer syndromes are of the tumor suppressor type. In such a circumstance, affected individuals have inherited one altered copy of the responsible gene from an affected parent (they are heterozygotes), but the tumors have lost the remaining functional copy (the "wild-type allele") as a somatic event (becoming non-functional homozygotes). Germ-line homozygocity would be fatal. Thus the inheritance pattern of the syndrome is dominant, but the mechanism of tumorigenesis is recessive.

Finding the gene responsible for such a cancer syndrome would provide a new window into the mechanism of tumorigenesis, would facilitate accurate early diagnosis, and would, through screening, identify individuals predisposed to cancer. In the case of MEN1, a patient in an affected kindred manifesting any one of the classic features of the syndrome is at risk for the development of the other associated tumors. According to standard medical practice, periodic screening of both affected individuals and unaffected relatives is considered essential. Standard practice recommends that this be done at least biannually and include, e.g., review of the history for symptoms suggestive of peptic ulcer disease, diarrhea, nephrolithiasis, hypoglycemia, and hypopituitarism; physical examination for features of acromegaly and subcutaneous lipomas; and measurement of serum Ca, phosphate (PO4), gastrin, and prolactin. Further laboratory testing, CT or MRI of the sella turcica, and other diagnostic maneuvers should also be performed when clinically indicated. Prior to this invention, no protein or gene-based diagnostic test was available.

The significance of discovering such a tumor suppressor gene extends beyond affected pedigrees, as the same tumor suppressor gene is often found to play a role (by somatic mutation of both alleles in individuals born homozygous for a wild-type, functional allele) in sporadic cases of various neoplasms. These non-hereditary tumors are typically endocrine tumors. Identification of non-hereditary mutations can give information about the origin of the tumor and its prognosis. Furthermore, treatments arising from the gene's discovery will lead to the amelioration and/or prevention of such tumors.

Thus, there exists a great need to identify the gene associated with MEN1 and FMEN1, as characterization such a gene which would allow identification of those individuals with MEN1, provide lifesaving diagnostic tests, therapeutic treatment regimens, and prognostic evaluations of individuals with FMEN1 and individuals with somatic mutations involving both alleles resulting in non-hereditary tumors. The present invention fulfills these and other needs.

BRIEF DESCRIPTION OF THE FIGURES

FIG. 1 shows the nucleotide sequence and of an apparently full length MEN1 cDNA as derived from a leukocyte cDNA clone (SEQ ID NO:1), and the corresponding predicted amino acid sequence (SEQ ID NO:2). The boundaries of the exons are shown, as identified by comparison with the complete genomic sequence of a 9.2 kb segment containing all 10 exons (SEQ ID NO:3). The first exon is completely untranslated. The ATG at nucleotide 111 is predicted to be the initiation codon, since it is associated with an excellent Kozak consensus sequence, and there are no other in-frame ATG codons upstream of this (an in-frame stop occurs at nucleotide 20). The stop codon (TGA) and the proposed polyadenylation signal sequence (AATACA) are boxed. The polyadenylation signal is a variant from the usual AATAAA, and appears located closer than usual to the string of adenosines; however, the first eight of these are also represented in genomic DNA.

FIG. 4 shows a summary of mutations identified in unrelated MEN1 patients. Abbreviations follow standard nomenclature (Beaudet (1993) supra)

SUMMARY OF THE INVENTION

Figure 2:
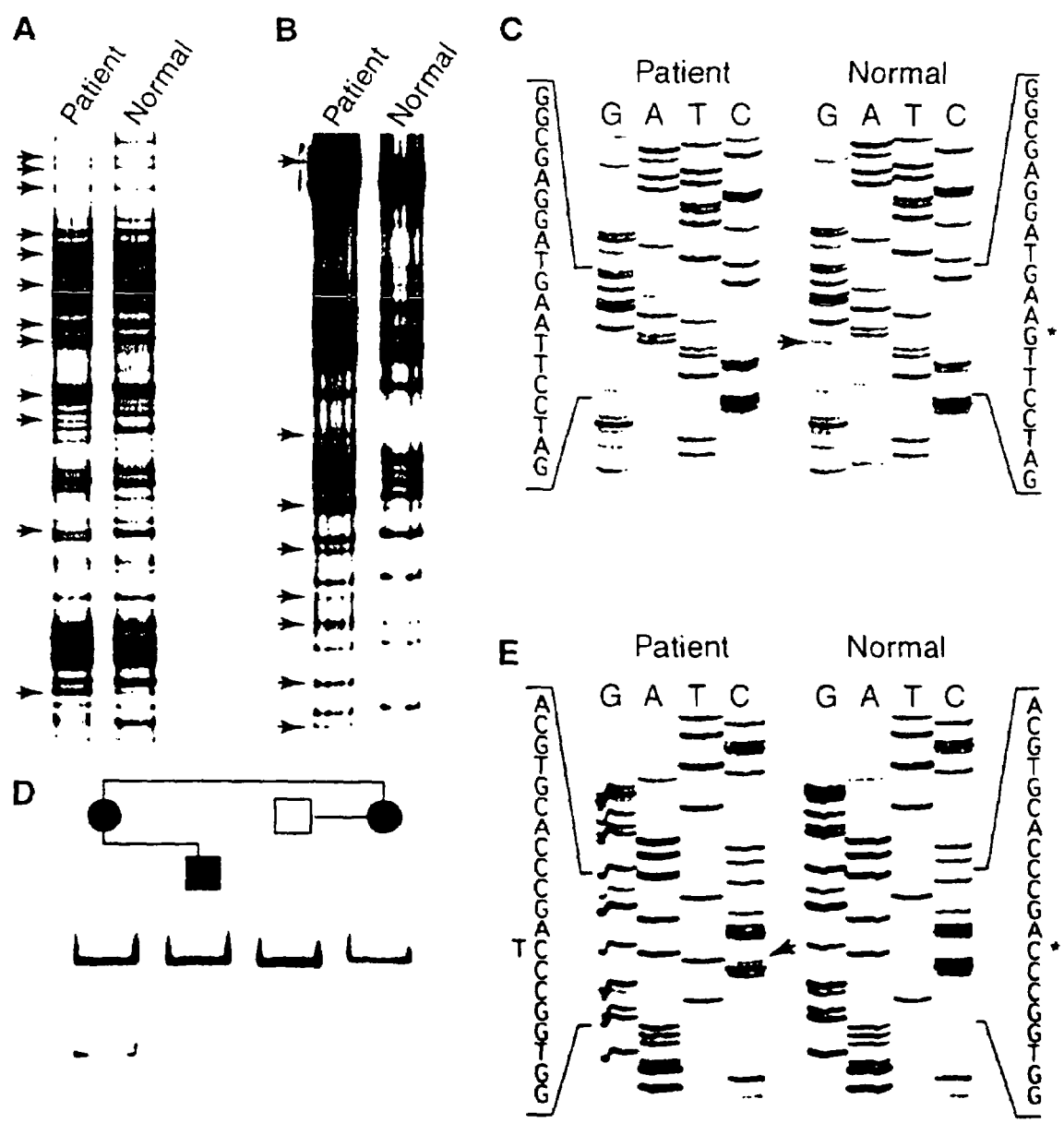
FIG. 2 shows the detection of frameshift and nonsense mutations. (A) Analysis of exon 2 in a MEN1 patient and a normal control, using dideoxy fingerprinting (ddF) to reveal pattern differences (arrows) indicative of a possible mutation. (B) Abnormal ddF pattern in exon 9 from a different patient. (C) Identification of a single nucleotide deletion by sequencing of a cloned exon 2 PCR product from the patient whose ddF pattern is shown in (A). The sequence shown (SEQ ID NO:4) is of the antisense strand; the mutation is 512delC (normal=SEQ ID NO:5). This frameshift mutation was confirmed by detecting the presence of a new AflII site in PCR-amplified exon 2 from this patient and two affected relatives (D). (E) Direct sequencing of the exon 9 PCR product from panel (B), revealing the presence of a heterozygous C to T (C=>T) substitution (SEQ ID NOS:6 and 7). Again the sequence is of the antisense strand; the mutation creates a stop codon: TGG to TAG or W436X (TGG=>TAG or W436X).

This invention provides for an isolated or recombinant nucleic acid associated with the presence of multiple endocrine neoplasia type 1, wherein said nucleic acid encodes a protein defined as having a calculated molecular weight of about 67.5 kDa; and (a) specifically binding to an antibody raised against an protein with a sequence as set forth in SEQ ID NO:2; or (b) having at least 60% amino acid sequence identity to a protein with a sequence as set forth in SEQ ID NO:2. In various embodiments, the isolated or recombinant nucleic acid can further comprises non-coding sequence; and the non-coding sequence can comprises introns. In one embodiment, the isolated or recombinant nucleic acid has the sequence as set forth in SEQ ID NO:3.

The invention also provides for an isolated or recombinant nucleic acid which encodes a protein having at least 80% amino acid sequence identity to a protein with a sequence as set forth in SEQ ID NO:2. In alternative embodiments, the isolated or recombinant nucleic acid encodes a menin protein with a sequence as set forth in SEQ ID NO:2, or, the isolated or recombinant nucleic acid has the sequence as set forth in SEQ ID NO:1.

This invention further provides for an isolated or recombinant protein defined as having a calculated molecular weight of about 67.5 kDa; and (a) specifically binding to an antibody raised against an protein with a sequence as set forth in SEQ ID NO:2; or (b) having at least 60% amino acid sequence identity to a protein with a sequence as set forth in SEQ ID NO:2. In various embodiments, the isolated or recombinant protein has at least 80% amino acid sequence identity to a protein with a sequence as set forth in SEQ ID NO:2; or, an isolated or recombinant protein having a sequence as set forth in SEQ ID NO:2.

The invention further provides for an antibody, specifically immunoreactive under immunologically reactive conditions, to a protein comprising SEQ ID NO:2; and, an antibody, specifically immunoreactive under immunologically reactive conditions, to a protein, wherein the protein is encoded by a nucleic acid encoding a protein defined as having a calculated molecular weight of about 67.5 kDa; and (a) specifically binding to an antibody raised against an protein with a sequence as set forth in SEQ ID NO:2; or (b) having at least 60% amino acid sequence identity to a protein with a sequence as set forth in SEQ ID NO:2.

This invention further provides for methods of detecting the presence of menin in human cells and tissues, said method comprising: (i) isolating a biological sample from a human being tested for menin; (ii) contacting the biological sample with a menin specific reagent; and, (iii) detecting the level of menin specific reagent that selectively associates with the sample. The method is contemplated for a variety of different purposes including sporadic (non-hereditary) cancers arising in any cell or tissue from mutations of MEN1 or loss of heterozygosity of wild type MEN1, as in multiple endocrine neoplasia type 1 (MEN1). The methods include nucleic acid hybridization technology, amplification of nucleic acid technology and immunoassays.

In various embodiments, in the method of detecting the presence of menin in human cells and tissues, the menin specific reagent is selected from the group comprising: menin specific antibodies, MEN1 amplification primers and nucleic acid probes which selectively bind to MEN1. In this method, the contacting step can also use a menin specific antibody. The human from which the sample is isolated is suspected of being at risk from multiple endocrine neoplasia type 1 (MEN1). In this method, the contacting step can use a MEN1 specific PCR primer pair that amplifies a region of the MEN1 gene in which a mutation has been associated with multiple endocrine neoplasia type 1 (MEN1).

The invention also provides for a method for detecting in a test sample the presence or absence of a mutation in a nucleotide sequence essentially encoding human menin comprising: contacting said test sample suspected of lacking a MEN1 allele or containing a gene encoding a mutant form of the human menin with a first oligonucleotide having a sequence competent to discriminate between the wild type gene and the missing MEN1 allele or mutant form; and, b) detecting the formation of a duplex between the gene and the first oligonucleotide sequence. Such assays would include those wherein the first oligonucleotide is unable to bind to the wild-type MEN1 gene under hybridization conditions in which the first nucleotide binds to the mutant sequence of MEN1.

This invention also provides for kits for detecting in a test sample the presence or absence of a mutation in a nucleotide sequence corresponding to the wild type allele encoding menin comprising: a) a container holding a first oligonucleotide sequence whereby said first nucleotide sequence is capable of discriminating between the wild type gene and the mutant form; and b) a container holding a reagent for detecting the formation of a duplex between the gene and the first nucleotide sequence. The kit can further comprising amplification primer pairs specifically binding to a human genomic DNA sequence containing MEN1.

The invention further provides for a kit for detecting the presence or absence of menin in persons at risk for multiple endocrine neoplasia type 1 comprising a first container containing at least one antibody specific for a wild type menin or a mutant menin, and a second container containing an antigen that specifically binds to the menin specific antibody in the first container. The antibody can detect the presence of a wild-type menin protein or the presence of a mutated menin protein. Kits for detecting any menin polypeptide aberration using immunoassays are also included in this invention for all of the various purposes recited above.

The invention also provides for a transfected cell comprising a heterologous nucleic acid encoding a menin protein or subsequence thereof. In one embodiment, the invention provides for a transfected cell into which an exogenous nucleic acid sequence has been introduced, the exogenous nucleic acid specifically hybridizing under stringent conditions to a nucleic acid with: a nucleic acid sequence as set forth in SEQ ID NO:1 or SEQ ID NO:3; or, a nucleic acid encoding a protein defined as having a calculated molecular weight of about 67.5 kDa; and (a) specifically binding to an antibody raised against an protein with a sequence as set forth in SEQ ID NO:2; or (b) having at least 60% amino acid sequence identity to a protein with a sequence as set forth in SEQ ID NO:2; and, the cell expresses the exogenous nucleic acid as a menin protein. The transfected cell of the invention can comprise a nucleic acid as set forth in SEQ ID NO:1 or SEQ ID NO:3. The transfected cell can be a human cell.

The invention provides for an organism into which an exogenous nucleic acid sequence has been introduced, the exogenous nucleic acid specifically hybridizing under stringent conditions to a nucleic acid with: a sequence as set forth in SEQ ID NO:1; or, a nucleic acid encoding a protein defined as having a calculated molecular weight of about 67.5 kDa; and (a) specifically binding to an antibody raised against an protein with a sequence as set forth in SEQ ID NO:2; or (b) having at least 60% amino acid sequence identity to a protein with a sequence as set forth in SEQ ID NO:2; and, the organism expresses the exogenous nucleic acid as a menin protein. In one embodiment, the organism comprises an exogenous nucleic acid as set forth in SEQ ID NO:1 or SEQ ID NO:3.

The invention also provides for an expression cassette comprising a nucleic acid encoding a menin polypeptide, wherein the nucleic acid is operably linked to a promoter and comprises a nucleic acid encoding a menin polypeptide. In one embodiment, the expression cassette further comprises an expression vector.

Finally, this invention also includes research uses for the MEN1 gene and its protein product, menin. Thus the detection of either the gene or gene product for detection of cells producing or suspected of producing menin are also contemplated for any use including simply identifying menin producing cells from non-menin producing cells such as animal or human cells from bacterial cells.

The invention also embraces the use of antisense methods for studying menin in animals and cells. Typically any time a gene is identified, it can be studied by knocking out the gene in an animal and observing the effect on the animal phenotype. Knockouts can be achieved by transposons which insert by homologous recombinations, antisense or ribozymes specifically directed at disturbing the embryonic stem cells of an organism such as a mouse. Ribozymes can include any of the various types of ribozymes modified to cleave the mRNA encoding menin. Examples include hairpins and hammerhead ribozymes. Finally antisense molecules which selectively bind to the menin mRNA are expressed via expression cassettes operably linked to subsequences of the menin gene and generally comprises 20-50 base long sequences in opposite orientation to the mRNA to which they are targeted.

DEFINITIONS

"Amplification" primers are oligonucleotides comprising either natural or analog nucleotides that can serve as the basis for the amplification of a select nucleic acid sequence. They include both polymerase chain reaction primers and ligase chain reaction oligonucleotides.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. Antibodies exist e.g., as intact immunoglobulins or as a number of well characterized fragments produced by digestion with various peptides. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

"Associated" in the context of multiple endocrine neoplasia type 1 refers to relationship of the MEN1 gene to the disease. In a classic sense, it is a suppressor gene. However it is not known if the effect of the mutation is direct or indirect upon the cell phenotype. Accordingly, we refer to the relationship as an association rather than a suppressor effect because of the lack of proof that (lack of a functional) MEN1 is directly responsible for the cancer phenotype. This fact in no way diminishes the use of the gene in diagnosing either multiple endocrine neoplasia type 1 (MEN1, see definition, below) per se, or a predisposition to multiple endocrine neoplasia type 1 in an individual at risk for this disease. Individuals at risk for the disease have only one functional MEN1 gene product (are heterozygotes for wild type MEN1), and have inherited the familial multiple endocrine neoplasia type 1 syndrome.

"Biological samples" refers to any tissue or liquid sample having a menin-encoding nucleic acid, including message or genomic DNA, or the MEN1 gene product. It includes both cells with a normal complement of chromosomes and cells suspected of bearing at least one oncogenic mutation, e.g., in MEN1.

"Competent to discriminate between the wild type gene and the mutant form" means a hybridization probe or primer sequence that allows the trained artisan to detect the presence or absence of base changes, deletions or additions to a wild type nucleotide sequence encoding menin. The term "wild type gene" includes all alleles encoding for a functional gene product, such as an MEN1 gene encoding a functional gene product, the menin polypeptide. A probe sequence is a sequence containing the site that is changed, deleted to or added to. A primer sequence will hybridize with the sequences surrounding or flanking the base changes, deletions or additions and using the gene sequence as template allow the further synthesis of nucleotide sequences that contain the base changes or additions. In addition, the probe may act as a primer. It is important to point out that this invention allows for the design of PCR primers capable to amplify entire exons. To achieve this, primers need hybridize with intron sequences. This invention provides such intron sequences. "Competent to discriminate between the wild type gene and the mutant form" also includes an immunoreactive reagent, e.g., an antibody, that allows the trained artisan to detect the presence or absence of a wild type (biologically active allele of) menin, as opposed to a non-functional menin.

The term "expression cassette" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression cassettes, e.g., vectors, that remain episomal or integrate into the host cell genome. The expression cassettes can have the ability to self-replicate or not, i.e., drive only transient expression in a cell. The term includes recombinant expression cassettes which contain only the minimum elements needed for transcription of the recombinant nucleic acid.

The phrase "genomic" refers to DNA which includes both the exon and intron regions as well as the untranslated sequences that are 5' exon 1 and 3' of exon 10 of the MEN1 gene. Intron 1 is between exon I and exon II, intron 2 is between exon II and exon III, intron 3 is between exon III and exon IV, and intron is between exon IV and exon V and so on. The term "genomic" also refers to any cis-acting transcriptional regulatory elements, e.g., promoters and enhancers, that regulate the expression of MEN1.

The term "isolated," when referring to a molecule or composition, such as, for example, a polypeptide or nucleic acid, means that the molecule or composition is separated from at least one other compound, such as a protein, other nucleic acids (e.g., RNAs), or other contaminants with which it is associated in vivo or in its naturally occurring state. Thus, a polypeptide or nucleic acid is considered isolated when it has been isolated from any other component with which it is naturally associated, e.g., cell membrane, as in a cell extract. An "isolated" composition can, however, also be substantially pure (substantially free of other cellular components). An "isolated" composition can be when the nucleic acid or protein is essentially free of other cellular components with which it is associated in the natural state. It can be in a homogeneous state, although it can also be in either a dry or aqueous solution. Purity and homogeneity are typically determined using analytical chemistry techniques such as polyacrylamide gel electrophoresis or high performance liquid chromatography. In one embodiment, the protein which is the predominant species present in a preparation is substantially purified. In particular, an isolated MEN1 gene is separated from open reading frames which flank the gene and encode a protein other than the MEN1 gene product. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"MEN1" refers to a gene encoding the polypeptide menin. There is an expectation that the human population has a normal degree of variance in this gene (wild-type alleles encoding for functional, biologically active menin). The genomic sequence of an exemplary wild-type MEN1 allele is set forth as SEQ ID NO:3, with the corresponding transcribed sequence (cDNA) as SEQ ID NO:1. The presence of mutations in MEN1, producing a nonfunctional MEN1 allele (incapable of producing a biologically active menin polypeptide) is associated with the presence of MEN1, a familial cancer syndrome.

"Menin" refers to a protein encoded by an MEN1 gene (allele). In its full length, wild-type form it is about 67.5 kilodaltons (kd), its theoretical molecular weight whose calculation is based on translation of the MEN1 gene nucleic acid sequence. The term "menin" includes a polypeptides which selectively bind to antibodies raised against a MEN1 gene product, e.g., SEQ ID NO:2, or are encoded by nucleic acid that would selectively hybridize to the exons of SEQ ID NO:3. "Wild-type menin" includes those allelic variants which could reverse the tumorigenic phenotype.

"Menin-specific reagent" is a composition of matter that binds to either menin (e.g., an antibody) or to MEN1 (e.g., nucleic acid probes and/or amplification primers).

"Multiple endocrine neoplasia-type 1," sometimes referred to as "MEN1" or "MEN I" or "Familial multiple endocrine neoplasia-type 1" or "FMEN1," refers a familial cancer syndrome in which affected individuals develop varying combinations of endocrine and non-endocrine tumors; including tumors of the parathyroids, pancreatic islets (insulinomas), duodenal endocrine cells, anterior pituitary, foregut carcinoids (gastrinomas), lipomas (non-endocrine), angiofibromas (non-endocrine), thyroid adenomas, adrenocortical adenomas, angiomyolipomas (non-endocrine), spinal cord ependymonas, neuroendocrine tumors of lung, thymus and stomach. Except for gastrinomas, most of the tumors are nonmetastasizing. Many have striking clinical effects because of the secretion of endocrine substances, such as gastrin, insulin, parathyroid, hormone, prolactin, growth hormone, glucagon, or adrenocorticotropic hormone. The clinical features of the MENI syndrome depend upon the pattern of tumor involvement in the individual patient. About 40% of reported cases have had tumors of the parathyroids, pancreas, and pituitary. Almost any combination of tumors and symptom complexes outlined above is possible.

MEN1 one type of "multiple endocrine neoplasias" (also called "Multiple Endocrine Adenomatosis, "MEA," or "Familial Endocrine Adenomatosis"), which are a group of genetically distinct familial diseases involving adenomatous hyperplasia and malignant tumor formation in several endocrine glands. Three distinct syndromes, MENI, MEN II and MEN III, have been identified; each is inherited as an autosomal dominant trait with a high degree of penetrance, variable expressivity, and significant pleiotropism. Prior to this invention, the relationship between the genetic abnormalities and the pathogenesis of the various tumors was not understood.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer (1991) *Nucleic Acid Res.* 19:5081; Ohtsuka (1985) *J. Biol. Chem.* 260:2605-2608; and Cassol (1992); Rossolini (1994) *Mol. Cell. Probes* 8:91-98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859-1862 (1981) (Beaucage and Carruthers), or by the triester method according to Matteucci (1981) *J. Am. Chem. Soc.,* 103:3185 (Matteucci). A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "a nucleic acid sequence encoding" refers to a nucleic acid which contains sequence information for a structural RNA such as rRNA, a tRNA, or the primary amino acid sequence of a specific protein or peptide. The term can also refer to a binding site for a trans-acting regulatory agent. This phrase specifically encompasses degenerate codons (i.e., different codons which encode a single amino acid) of the native sequence or sequences which may be introduced to conform with codon preference in a specific host cell.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to a wild-type menin, such as menin with the amino acid sequence encoding in SEQ ID NO:2, can be selected to obtain antibodies (polyclonal or monoclonal) specifically immunoreactive with all wild-type menin proteins and not with non-menin proteins. Antibodies can also be raised to react only with a specific wild-type polymorphic variant of menin (encoded by an MEN1 allele). A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual,* Cold Spring Harbor Publications, New York "Harlow and Lane"), for a description of immunoassay formats and conditions that can be used to determine specific immunoreactivity. As used herein, a specific or selective reaction will be at least twice background signal or noise, although typically it can be more than 10 to 100 times background.

The phrases "hybridizing specifically to" or "hybridizing selectively to" or "selectively or specifically hybridizes", refers to the binding, duplexing, or hybridizing of a nucleic acid molecule preferentially to a particular nucleotide sequence under stringent conditions when that sequence is present in a complex mixture (e.g., total cellular) DNA or RNA. "Stringent hybridization" or "stringent conditions" and "stringent hybridization wash conditions" in the context of nucleic acid hybridization experiments, e.g., Southern and Northern hybridizations, are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or Northern blot is 50% formalin with 1 mg of heparin at 42° C., with the hybridization being carried out overnight. An example of highly stringent wash conditions is: 0.15M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. As used herein, a signal to noise ratio of 2× (or higher) than that observed for an unrelated probe in the particular hybridization assay indicates detection of a specific hybridization. Nucleic acids which do not hybridize to each other under stringent conditions can still be substantially identical if the polypeptides which they encode are substantially identical. This occurs, e.g., when a copy of a nucleic acid is created using the maximum codon degeneracy permitted by the genetic code.

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison (see detailed discussion, below). The reference sequence may be a subset of a larger sequence.

As applied to polypeptides such as menin, the terms "substantial identity" or "substantial sequence identity" mean that two peptide sequences, when optimally aligned, such as by the programs of GAP or BESTFIT using default gap weights (see detailed discussion, below), share at least 70 percent sequence identity, preferably at least 80 percent sequence identity, more preferably at least 90 percent sequence identity, and most preferably at least 95 percent amino acid identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optionally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

DETAILED DESCRIPTION

This invention is the discovery that the presence of mutations in the gene designated MEN1 are associated with individuals that are at risk for sporadic cancers, including sporadic endocrine cancers, and diseases including multiple endocrine neoplasias. These mutations can result in lack of expression of a protein, expression of a nonfunctional protein form, or significant underexpression of a functional form. Below we teach how to obtain and identify an MEN1 gene allele. Also taught is how to express and purify the MEN1 gene product menin, including a description of the various conventional methods one could use to detect and quantify the expression and quality of menin.

Sequencing of DNA from MEN-I affected individuals allowed us to identify both a wild-type MEN1 allele and many mutated forms of MEN1. The mutated gene can be the result of a variety of different frameshift, nonsense, missense, and/or in-frame deletion mutations; analysis of mutated forms of MEN1 isolated from affected individuals are summarized in FIGS. 3 and 4.

The wild-type, functional MEN1 gene contains 10 exons and extends across 9 kb. It appears that the MEN1 gene is ubiquitously expressed as a 2.8 kb transcript. The predicted 610 amino acid protein product, for which we propose the name "menin", exhibits no apparent similarities with any previously known proteins.

The identification of the MEN1 gene provides a new window into the mechanism of endocrine tumorigenesis, facilitates accurate early diagnosis of MEN1 associated cancers, and provides preclinical identification of individuals with the FMEN1 syndrome, i.e., cancer free individuals that are at high risk of acquiring (predisposed to) MEN1 associated tumors.

Cloning, Analysis and Expression of the MEN1 Gene

A. General Recombinant DNA Methods

This invention relies on routine techniques in the field of recombinant genetics. A basic text disclosing the general methods of use in this invention is Sambrook et al., *Molecular Cloning, A Laboratory Manual,* Cold Spring Harbor Publish., Cold Spring Harbor, N.Y. 2nd ed. (1989) and Kriegler, *Gene Transfer and Expression: A Laboratory Manual,* W. H. Freeman, N.Y., (1990). Unless otherwise stated all enzymes are used in accordance with the manufacturer's instructions.

Nucleotide sizes are given in either kilobases (Kb) or base pairs (bp). These are estimates derived from agarose or acrylamide gel electrophoresis or from published DNA sequences.

Oligonucleotides that are not commercially available can be chemically synthesized according to the solid phase phosphoramidite triester method first described by S. L. Beaucage and M. H. Caruthers, *Tetrahedron Letts.,* 22(20): 1859-1862 (1981) using an automated synthesizer, as described in D. R. Needham Van Devanter et. al., *Nucleic Acids Res.,* 12:6159-6168, 1984. Purification of oligonucleotides is by either native acrylamide gel electrophoresis or by anion-exchange HPLC as described in J. D. Pearson and F. E. Reanier, *J. Chrom.,* 255:137-149, 1983.

The sequence of the cloned genes and synthetic oligonucleotides can be verified using the chemical degradation method of A. M. Maxam et al., *Methods in Enzymology,* 65:499560, (1980). The sequence can be confirmed after the assembly of the oligonucleotide fragments into the double-stranded DNA sequence using the method of Maxam and Gilbert, supra, or the chain termination method for sequencing double-stranded templates of R. B. Wallace et al. *Gene,* 16:21-26, 1981. Southern blot hybridization techniques are carried out according to Southern et al., *J. Mol. Biol.,* 98:503, 1975.

B. Cloning Methods for the Isolation of Nucleotide Sequences Encoding Menin Proteins In general, the nucleic acid sequences encoding menin are cloned from DNA sequence libraries that are made to encode copy DNA (cDNA) or genomic DNA. The particular sequences can be located by hybridizing with an oligonucleotide probe, the sequence of which can be derived from table 1 which provides PCR primers and defines suitable regions for isolating MEN1 specific probes. Alternatively, where the sequence is cloned into an expression library, the expressed recombinant menin be detected immunologically with antisera or purified antibodies made against menin.

To make the cDNA library, one should choose a source that is rich in mRNA. For example, liver is enriched for mRNA of menin. The mRNA can then be made into cDNA, ligated into a recombinant vector, and transfected into a recombinant host for propagation, screening and cloning. Methods for making and screening cDNA libraries are well known. See Gubler, U. and Hoffman, B. J. *Gene* 25:263-269, 1983 and Sambrook.

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro, as described in Sambrook. Recombinant phage are analyzed by plaque hybridization as described in Benton and Davis, *Science,* 196:180-182 (1977). Colony hybridization is carried out as generally described in M. Grunstein et al. *Proc. Natl. Acad. Sci. USA.,* 72:3961-3965 (1975).

An alternative method combines the use of synthetic oligonucleotide primers with polymerase extension on an mRNA or DNA template. This polymerase chain reaction (PCR) method amplifies nucleic acid sequences of MEN1 directly from mRNA, from cDNA, from genomic libraries or cDNA libraries. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of menin encoding mRNA in physiological samples, for nucleic acid sequencing, or for other purposes. U.S. Pat. Nos. 4,683,195 and 4,683,202 describe this method. Genes amplified by the PCR reaction can be purified from agarose gels and cloned into an appropriate vector. Appropriate primers and probes for identifying MEN1 genes encoding menin protein from alternative mammalian biological samples, including cells and tissues, are generated from comparisons of the sequences provided herein. For a general overview of PCR see *PCR Protocols: A Guide to Methods and Applications* (Innis, M, Gelfand, D., Sninsky, J. and White, T., eds.), *Academic Press,* San Diego (1990).

Synthetic oligonucleotides can be used to construct MEN1 genes. For example, this can be done using a series of overlapping oligonucleotides usually 40 to 120 bp in length, representing both the sense and nonsense strands of the gene. These DNA fragments are then annealed, ligated and cloned.

The gene for menin can be cloned using intermediate vectors before transformation into mammalian cells for expression. These intermediate vectors are typically prokaryote vectors or shuttle vectors. Menin can be expressed in either prokaryotes or eukaryotes.

In summary, the menin gene can identified and prepared by probing or amplifying select regions of a biological sample, such as a mixed cDNA or genomic pool, using the probes and primers generated from the MEN1 sequences; exemplary probes are provided herein in Table 1 (sequence numbering based on SEQ ID NO:3).

ment of sequences for comparison can use any means to analyze sequence identity (homology) known in the art, e.g., by the progressive alignment method of termed "PILEUP" (see below); by the local homology algorithm of Smith & Waterman (1981) *Adv. Appl. Math.* 2: 482; by the homology alignment algorithm of Needleman & Wunsch (1970) *J. Mol. Biol.* 48:443; by the search for similarity method of Pearson (1988) *Proc. Natl. Acad. Sci. USA* 85: 2444; by computerized implementations of these algorithms (e.g., GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif.), described by, e.g., Higgins (1988) *Gene* 73: 237-244; Corpet (1988) *Nucleic Acids Res.* 16:10881-90; Huang (1992) *Computer Applications in the Biosciences* 8:155-65, and Pearson (1994) *Methods in Molec. Biol.* 24:307-31). Other sequence alignment computer programs include Pfam (Sonnhammer (1998) *Nucleic Acids Res.* 26:322-325); Tree-Align (Hein (1994) *Methods Mol. Biol.* 25:349-364); MES-ALIGN, and SAM programs; or, visual inspection can identify sequence identities.

TABLE 1

| Exons | Primary PCR primers | Product size(bp) | ddF primers |
|---|---|---|---|
| Exon 2 from ATG | MEN2A(1932-1953) (SEQ ID NO:8) gacctgggtgcgctttctggac<br>MEN2B(2946-2968) (SEQ ID NO:9) gaggtgaggttgatgatttggag | 1039 | MEN2C(2451-2473) (SEQ ID NO:10) ggtgagctcgggaacgttggtag<br>MEN2D(2629-2652) (SEQ ID NO:11) gagaccttcttcaccagctcacgg<br>MEN2E(2810-2833) (SEQ ID NO:12) cgaacctcacaaggcttacagttc |
| Exon 3 | MEN3A(4096-4119) (SEQ ID NO:13) gttggacatagagggtgtaaacag<br>MEN3B(5497-5520) (SEQ ID NO:14) acagttgacacaaagtgagactgg | 1427 | MEN3C(4613-4637) (SEQ ID NO:15) ggctcttctgtcttcccttcctatg |
| Exon 4 | MEN3A(4096-4119) (SEQ ID NO:13) gttggacatagagggtgtaaacag<br>MEN3B(5497-5520) (SEQ ID NO:14) acagttgacacaaagtgagactgg | 1427 | MEN4C(4881-4904) (SEQ ID NO:16) ggtcccacagcaagtcaagtctgg |
| Exon 5 | MEN3A(4096-4119) (SEQ ID NO:13) gttggacatagagggtgtaaacag<br>MEN3B(5497-5520) (SEQ ID NO:14) acagttgacacaaagtgagactgg | 1427 | MEN5C(5138-5161) (SEQ ID NO:17) cctgttccgtggctcataactctc |
| Exon 6 | MEN3A(4096-4119) (SEQ ID NO:13) gttggacatagagggtgtaaacag<br>MEN3B(5497-5520) (SEQ ID NO:14) acagttgacacaaagtgagactgg | 1427 | MEN5C(5138-5161) (SEQ ID NO:17) cctgttccgtggctcataactctc |
| Exon 7 | MEN7A(5828-5849) (SEQ ID NO:18) cctcagccagcagtcctgtaga<br>MEN7B(6212-6233) (SEQ ID NO:19) ggacgagggtggttggaaactg | 408 | MEN7C(5911-5933) (SEQ ID NO:20) ggactccttgggatcttcctgtg |
| Exon 8 | MEN8A(6404-6425) (SEQ ID NO:21) aacgaccatcatccagcagtgg<br>MEN8B(6834-6855) (SEQ ID NO:22) ccatccctaatcccgtacatgc | 454 | MEN8C(6577-6600) (SEQ ID NO:23) tggtgagacccccttcagacctac |
| Exon 9 | MEN9A(7142-7164) (SEQ ID NO:24) ctgctaaggggtgagtaagagac<br>MEN9B(8190-8212) (SEQ ID NO:25) ggtttgatacagactgtactcgg | 1073 | MEN9C(7404-7426) (SEQ ID NO:26) gtctgacaagcccgtggctgctg |
| Exon 10 to stop | MEN9A(7142-7164) (SEQ ID NO:24) ctgctaaggggtgagtaagagac<br>MEN9B(8190-8212) (SEQ ID NO:25) ggtttgatacagactgtactcgg | 1073 | MEN10C(7445-7467) (SEQ ID NO:27) gcatctgcccatcccttcggtg<br>MEN10D(7775-7797) (SEQ ID NO:28) gaagcctcctgggactgtcgctg |

C. Analysis of Menin-encoding Nucleic Acid Sequences

The menin polypeptide encoding nucleic acid sequences of the invention includes genes and gene products identified and characterized by analysis using the sequences nucleic acid and protein sequences of the invention, including SEQ ID NO:1 and SEQ ID NO:2, respectively. Optimal align- One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351-360, see also the method of Higgins & Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. See also Morrison (1997) *Mol. Biol. Evol.* 14:428-441, as an example of the use of PILEUP.

Another example of algorithm that is suitable for determining sequence similarity is the BLAST algorithm, which is described in Altschul (1990) *J. Mol. Biol.* 215: 403-410. Software for performing BLAST analyses is publicly available through the National Center for Biotechnology Information, http://www.ncbi.nlm.nih.gov/; see also Zhang (1997) *Genome Res.* 7:649-656 (1997) for the "PowerBLAST" variation. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word his are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992) *Proc. Natl. Acad. Sci. USA* 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993) *Proc. Natl. Acad. Sci. USA* 90:5873-5787. One measure of similarity provided by the BLAST algorithm is the smallest sum probability (P(N)), which provides an indication of the probability by which a match between two nucleotide or amino acid sequences would occur by chance.

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

D. Sequencing of Menin-Encoding Nucleic Acid

Sequencing of isolated menin-encoding nucleic acid is used, e.g., to identify and characterize wild-type allelic variations; to identify mutations found in vivo or generated in vitro; to confirm sequence of cloned or amplified nucleic acid; and the like. Menin-encoding sequences can be sequenced as inserts in vectors, as inserts released and isolated from the vectors or in any of a variety of other forms (i.e., as amplification products). Menin-encoding inserts can be released from the vectors by restriction enzymes or amplified by PCR or transcribed by a polymerase. For sequencing of the inserts to identify full length coding sequences, primers based on the N- or C-terminus, or based on insertion points in the original phage or other vector, can be used. Additional primers can be synthesized to provide overlapping sequences. Nucleic acid sequencing techniques were all known, see, e.g. Rosenthal (1987) supra; Arlinghaus (1997) *Anal. Chem.* 69:3747-3753; Dubiley (1997) *Nucleic Acids Res.* 25:2259-2265, for use of biosensor chips for identification and sequencing of nucleic acids.

E. Expression in Prokaryotes

To obtain high level expression of a cloned gene, such as those cDNAs encoding menin in a prokaryotic system, it is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsy, C., *J. Bacteriol.*, 158: 1018-1024 (1984), and the leftward promoter of phage lambda ($P_L$) as described by Herskowitz, I. and Hagen, D., *Ann. Rev. Genet.*, 14:399-445 (1980).

Expression systems for expressing the menin protein are available using a variety of bacteria including *E. coli, Bacillus* sp. and *Salmonella* (Palva (1983) *Gene* 22:229-235 (1983); Mosbach (1983) *Nature,* 302:543-545.

F. Expression in Eukaryotes

Standard eukaryotic transfection methods are used to produce mammalian, yeast or insect cell lines which express large quantities of menin protein which are then purified using standard techniques. See, e.g., Colley (1989) *J. Biol. Chem.* 264:17619-17622, and Guide to Protein Purification, in Vol. 182 of *Methods in Enzymology* (Deutscher ed., 1990). Transformations of eukaryotic cells are performed according to standard techniques as described by, e.g., Morrison (1977) *J. Bact.,* 132:349-351; Clark-Curtiss (1983) *Methods in Enzymology* 101:347-362.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see Sambrook et al., supra). It is only necessary that the particular genetic engineering procedure utilized be capable of successfully introducing at least one gene into the host cell which is capable of expressing the menin protein.

The particular eukaryotic expression vector used to transport the genetic information into the cell is not particularly critical. Any of the conventional vectors used for expression in eukaryotic cells may be used. Expression vectors containing regulatory elements from eukaryotic viruses are typically used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$. pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors of the invention can include selectable markers which result in gene amplification such as thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with a menin encoding sequence under the direction of the polyhedrin promoter or other strong baculovirus promoters.

The expression vector of the present invention can also contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprises a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see, e.g., Sambrook, supra, Ch. 16.

The prokaryotic elements that are typically included in the mammalian expression vector includes a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains at least one eukaryotic transcription unit or expression cassette that contains all the elements required for the expression of the menin encoding DNA in eukaryotic cells. A typical expression cassette contains a promoter operably linked to the DNA sequence encoding menin and signals required for efficient polyadenylation of the transcript. Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Additional elements of the cassette may include enhancers and, if genomic DNA is used as the structural gene, introns with functional splice donor and acceptor sites. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, e.g., *Enhancers and Eukaryotic Expression,* Cold Spring Harbor Pres, Cold Spring Harbor, N.Y. 1983. In the construction of the expression cassette, the promoter is preferably positioned about the same distance from the heterologous transcription start site as it is from the transcription start site in its natural setting. As is known in the art, however, some variation in this distance can be accommodated without loss of promoter function. In addition to a promoter sequence, the expression cassette should also contain a transcription termination region downstream of the structural gene to provide for efficient termination. The terminal region may be obtained from the same gene as the promoter sequence or may be obtained from different genes. If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The menin of the invention can also be expressed as a recombinant protein with one or more additional polypeptide domains linked thereto to facilitate protein detection, purification, or other applications. Such detection and purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp. Seattle, Wash.). The inclusion of a cleavable linker sequences such as Factor Xa or enterokinase (Invitrogen, San Diego, Calif.) between the purification domain and menin protein(s) may be useful to facilitate purification. An exemplary expression vector provides for expression of a menin fusion protein comprising the sequence encoding menin and nucleic acid sequence encoding six histidine residues followed by thioredoxin and an enterokinase cleavage site. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the patent and scientific literature, see e.g., Kroll (1993) DNA Cell. Biol, 12:441-53).

The DNA sequence encoding the menin can also be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*.

G. Expression in Cell Cultures

Menin cDNA can be ligated to various expression vectors for use in transforming host cell cultures. The vectors typically contain gene sequences to initiate transcription and translation of the menin gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of the menin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines. NIH 3T3 or COS cells are preferred.

As indicated above, the vector, e.g., a plasmid, which is used to transform the host cell, preferably contains DNA sequences to initiate transcription and sequences to control the translation of the menin gene sequence. These sequences are referred to as expression control sequences. Illustrative expression control sequences are obtained from the SV-40 promoter (*Science,* 222:524-527, (1983)), the CMV I.E. Promoter (*Proc. Natl. Acad. Sci.* 81:659-663, (1984)) or the metallothionein promoter (*Nature* 296:39-42, (1982)). The cloning vector containing the expression control sequences is cleaved using restriction enzymes and adjusted in size as necessary or desirable and ligated with sequences encoding menin by means well known in the art.

As with yeast, when higher animal host cells are employed, polyadenylation or transcription terminator sequences from known mammalian genes need to be incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, J. et al., *J. Virol.* 45: 773-781, (1983)).

Additionally, gene sequences to control replication in the host cell may be incorporated into the vector such as those found in bovine papilloma virus type-vectors. Saveria-Campo, M., "*Bovine Papilloma virus DNA a Eukaryotic Cloning Vector*" in DNA Cloning Vol. II a Practical Approach Ed. D. M. Glover, IRL Press, Arlington, Va. pp. 213-238, (1985).

The transformed cells are cultured by means well known in the art. For example, as published in *Biochemical Methods in Cell Culture and Virology,* Kuchler, R. J., Dowden, Hutchinson and Ross, Inc., (1977). The expressed G-6-Pase protein is isolated from cells grown as suspensions or as monolayers. The latter are recovered by well known mechanical, chemical or enzymatic means.

1. Expression in Yeast

Synthesis of heterologous proteins in yeast is well known and described *Methods in Yeast Genetics,* Sherman, F., et al., Cold Spring Harbor Laboratory, (1982) is a well recognized work describing the various methods available to produce menin in yeast.

For high level expression of a gene in yeast, it is essential to connect the gene to a strong promoter system as in the prokaryote and also to provide efficient transcription termination/polyadenylation sequences from a yeast gene. Examples of useful promoters include GAL1,1O (Johnson (1984) *Mol. and Cell. Biol.* 4:1440-1448) ADH2 (Russell (1983) *J. Biol. Chem.* 258:2674-2682), PHO5 (*EMBO J.* 6:675-680, (1982)), and MF alpha-1. A multicopy plasmid with a selective marker such as Leu-2, URA-3, Trp-1, and His-3 is also desirable. The MF alpha-1 promoter is preferred for expression of menin in yeast. The MF alpha-1 promoter, in a host of the alpha mating-type is constitutive, but is switched off in diploids or cells with the a mating-type. It can, however, be regulated by raising or lowering the temperature in hosts which have a ts mutation at one of the SIR loci. The effect of such a mutation at 35° C. on an alpha type cell is to turn on the normally silent gene coding for the alpha mating-type. The expression of the silent a mating-type gene, in turn, turns off the MF alpha-1 promoter. Lowering the temperature of growth to 27° C. reverses the whole process, i.e., turns the a mating-type off and turns the MF alpha-1 on (Herskowitz, I. and Oshima, Y., in *The Molecular Biology of the Yeast Saccharomyces,* (eds. Strathern, J. N. Jones, E. W., and Broach, J. R., Cold Spring Harbor Lab., Cold Spring Harbor, N.Y., pp. 181-209, (1982). The polyadenylation sequences are provided by the 3'-end sequences of any of the highly expressed genes, like ADH1, MF alpha-1, or TPI (Alber, T. and Kawasaki, G., *J. of Mol. & Appl. Genet.* 1:419-434, (1982).

A number of yeast expression plasmids like YEp6, YEp13, YEp4 can be used as vectors. A gene of interest can be fused to any of the promoters in various yeast vectors. The above-mentioned plasmids have been fully described in the literature, e.g., Botstein (1979) *Gene* 8:17-24; Broach (1979) *Gene,* 8:121-133.

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by, e.g. Beggs (1978) *Nature* 275:104-109; Hinnen (1978) *Proc. Natl. Acad. Sci. USA* 75:1929-1933. The second procedure does not involve removal of the cell wall. Instead the cells are treated with lithium chloride or acetate and PEG and put on selective plates (Ito, H., et al., *J. Bact.,* 153:163-168, (1983)).

Menin can be isolated from yeast by lysing the cells and applying standard protein isolation techniques to the lysates. The monitoring of the purification process can be accomplished by using Western blot techniques or radioimmunoassays.

3. Expression in Insect Cells

In one embodiment, recombinant menin of the invention is expressed in insect cells infected with an expression vector, such as baculovirus. The baculovirus expression vector utilizes the highly expressed and regulated

*Autographa californica* nuclear polyhedrosis virus (AcM-NPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding menin is inserted into a transfer plasmid vector in the proper orientation downstream from the polyhedrin promoter, and flanked on both ends with baculovirus sequences. Cultured insect cell, commonly *Spodoptera frugiperda,* are transfected with a mixture of viral and plasmid DNAs. The virus that develop, some of which are recombinant virus that result from homologous recombination between the two DNAs, are plated at 100-1000 plaques per plate. The plaques containing recombinant virus can be identified visually because of their ability to form occlusion bodies or by DNA hybridization. The recombinant virus is isolated by plague purification. The resulting recombinant virus, capable of expressing menin, is self propagating in that no helper virus is required for maintenance or replication. After infecting an insect culture with recombinant virus, one can expect to find recombinant protein within 48-72 hours. The infection is essentially lytic within 4-5 days. There are a variety of transfer vectors into which the MEN1 can be inserted. For a summary of transfer vectors see, e.g., Luckow (1988) *Bio/Technology* 6:47-55. In one embodiment, the transfer vector pAcUW21 described by Bishop (1992) *Seminars in Virology* 3:253-264, is used.

In a preferred embodiment, the insect expression system for the production of human menin utilizes *Drosophila* Schneider 2 cells (Schneider (1972) *J. Embryol. Exp. Morph.* 27:363-365) transfected with an appropriate vector containing the menin cDNA of the invention. In one embodiment, the pMT/V5-His vector is used; it contains an inducible metallothionein promoter for regulated transcription of insert (i.e., menin) RNA (Johansen (1989) *Genes and Develop,* 3:882-889). pMT/V5-His also contains a sequence encoding six histidines linked to the carboxy terminus of menin in order to facilitate purification of the menin protein. In various embodiments, restriction sites are added to the menin cDNA using, e.g., PCR, prior to insertion into compatable restriction sites in the selected expression vector, e.g., the pMT/V5-His vector. S2 cells can be transiently or stably transfected with the pMT/V5-His menin vector. In the latter case, a selection plasmid, pCoHYGRO (van der Straten (1989) *Curr. Methods Mol. Cell. Biol.* 1:1-8), must be co-transfected into S2 cells to produce stable cells under the antibiotic selection of hygromycin-B. S2 cells are grown at 23° C. in DES Expression Medium supplemented with 2 mM L-glutamine. To characterize and isolate the recombinantly expressed human menin polypeptide, the cells are harvested and lysed in a buffer containing 50 mM Tris HCl (pH 7.8), 150 mM NaCl and 1% Nonidet P-40 (Invitrogen Corp., Carlsbad, Calif.).

Two major advantages of the insect expression systems, compared to mammalian cell expression systems, are: that the insect (e.g, *Drosophila*) system does not require isolation of clones; and, hundreds of copies of the recombinant plasmid usually become integrated into the *Drosophila* genome, resulting in higher levels of expression of the polypeptide encoded by the vector insert (Kirkpatrick (1995) *J. Biol. Chem.* 270:19800-1980).

3. Expression in Mammalian Cells

The invention provides for expression of MEN1 encoding nucleic acids in mammalian cells, in vitro and in vivo, for both the production of recombinant menin and reconstitution of menin activity, for, e.g., experimental or therapeutic purposes. A variety of human diseases may be treated by gene therapy approaches that involve stably introducing a gene into a human cell such that the gene may be transcribed and the gene product may be produced in the cell, as discussed in detail below. MEN1 encoding nucleic acids can be inserted any expression cassette/expression vector using any technique known in the art: a few exemplary systems and methods are provided herein.

Expression in Recombinant Vaccinia Virus-infected Cells

The gene encoding menin can be inserted into a plasmid designed for producing recombinant vaccinia, such as pGS62, Langford (1986) *Mol. Cell. Biol.* 6:3191-3199. This plasmid consists of a cloning site for insertion of foreign genes, the P7.5 promoter of vaccinia to direct synthesis of the inserted gene, and the vaccinia TK gene flanking both ends of the foreign gene. When the plasmid containing MEN1 is constructed, the gene can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign gene inserted into the viral TK gene, thus rendering the TK gene inactive. Cells containing recombinant viruses are selected by adding medium containing 5-bromodeoxyuridine, which is lethal for cells expressing a TK gene. Confirmation of production of recombinant virus can be achieved by DNA hybridization using cDNA encoding the menin protein and by immunodetection techniques using antibodies specific for the expressed protein. Virus stocks may be prepared, e.g., by infection of cells such as HeLA S3 spinner cells and harvesting of virus progeny.

Purification of Menin

A number of conventional procedures can be employed when recombinant or synthetic menin is being purified. After expression or chemical synthesis, menin may be purified to substantial purity by standard techniques, including, e.g.: selective precipitation with such substances as ammonium sulfate; column chromatography; immunopurification methods; and others. See, for instance, R. Scopes, *Protein Purification: Principles and Practice,* Springer-Verlag: New York (1982), U.S. Pat. No. 4,673,641, Ausubel, and Sambrook. For example proteins having established molecular adhesion properties can be reversibly fused (chemically joined) to the menin (see discussion on fusion protein, supra). With the appropriate ligand, the menin can be selectively adsorbed to a purification column and then freed from the column in a relatively pure form. The fused/joined non-menin protein is then removed, e.g., by enzymatic activity, chemical reduction. Menin can also be purified using immunoaffinity columns.

A. Purification of Menin from Recombinant Bacteria

When recombinant proteins are expressed by the transformed bacteria in large amounts, typically after promoter induction; but expression can be constitutive, the proteins may form insoluble aggregates. There are several protocols that are suitable for purification of menin inclusion bodies.

For example, purification of aggregate proteins (hereinafter referred to as inclusion bodies) typically involves the extraction, separation and/or purification of inclusion bodies by disruption of bacterial cells, typically but not limited by, incubation in a buffer of about 100-150 µg/mL lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel and Sambrook and will be apparent to those of skill in the art. The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art. Following the washing step, the inclusion bodies are solubilized by the addition of a solvent that is both a strong hydrogen acceptor and a strong hydrogen donor (or a combination of solvents each having one of these properties); the proteins that formed the inclusion bodies may then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active menin. After solubilization, the protein can be separated from other bacterial proteins by standard separation techniques.

Alternatively it is possible to purify menin from bacteria periplasm. Where menin protein is exported into the periplasm of the bacteria, the periplasmic fraction of the bacteria can be isolated by cold osmotic shock in addition to other methods known to skill in the art (see Ausubel). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Menin

1. Solubility Fractionation

Often as an initial step and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

Menin has a calculated molecular weight of 67.5 kilodaltons and this knowledge can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

Menin can also be separated from other proteins on the basis of their size, net surface charge, hydrophobicity and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Detection and Analysis of MEN1

As should be apparent to those of skill, the invention is the identification of the MEN1 gene, the menin polypeptide, the association of mutations in the MEN1 gene with a predisposition to cancer and benign tumors (the heterozygote with one wild-type functional MEN1 allele and one non-functional MEN1 allele), and the presence of no MEN1 allele capable of producing a functional menin polypeptide in cancerous cells (uncontrolled cell growth caused by loss of heterozygosity (LOS), i.e., loss of the one remaining wild-type functional allele). The invention is also the discovery that there are many different pedigrees of MEN1 loss of function mutations, i.e., different patients suffering from multiple endocrine neoplasia type 1 (MEN1) have different mutations in their MEN1 gene. Accordingly, the present invention also includes methods for detecting the presence, alteration or absence of MEN1 DNA or RNA, or the presence or absence of a functional or non-functional menin polypeptide, in a physiological specimen. The methods of the invention determine the MEN1 genotype of the individual, and thus the risk of acquiring disease associated with mutations to MEN1.

Although any tissue having cells bearing the genome of an individual can be used, the most convenient specimen will be blood samples or biopsies of suspect tissue bearing the germline or somatic DNA of an individual. It is also possible and preferred in some circumstances to conduct assays on cells that are isolated under microscopic visualization. A particularly useful method is the microdissection technique described in PCT application WO/95/23960. The cells isolated by microscopic visualization can be used in any of the assays described herein including both genomic and immunologic based assays.

Figure 1:
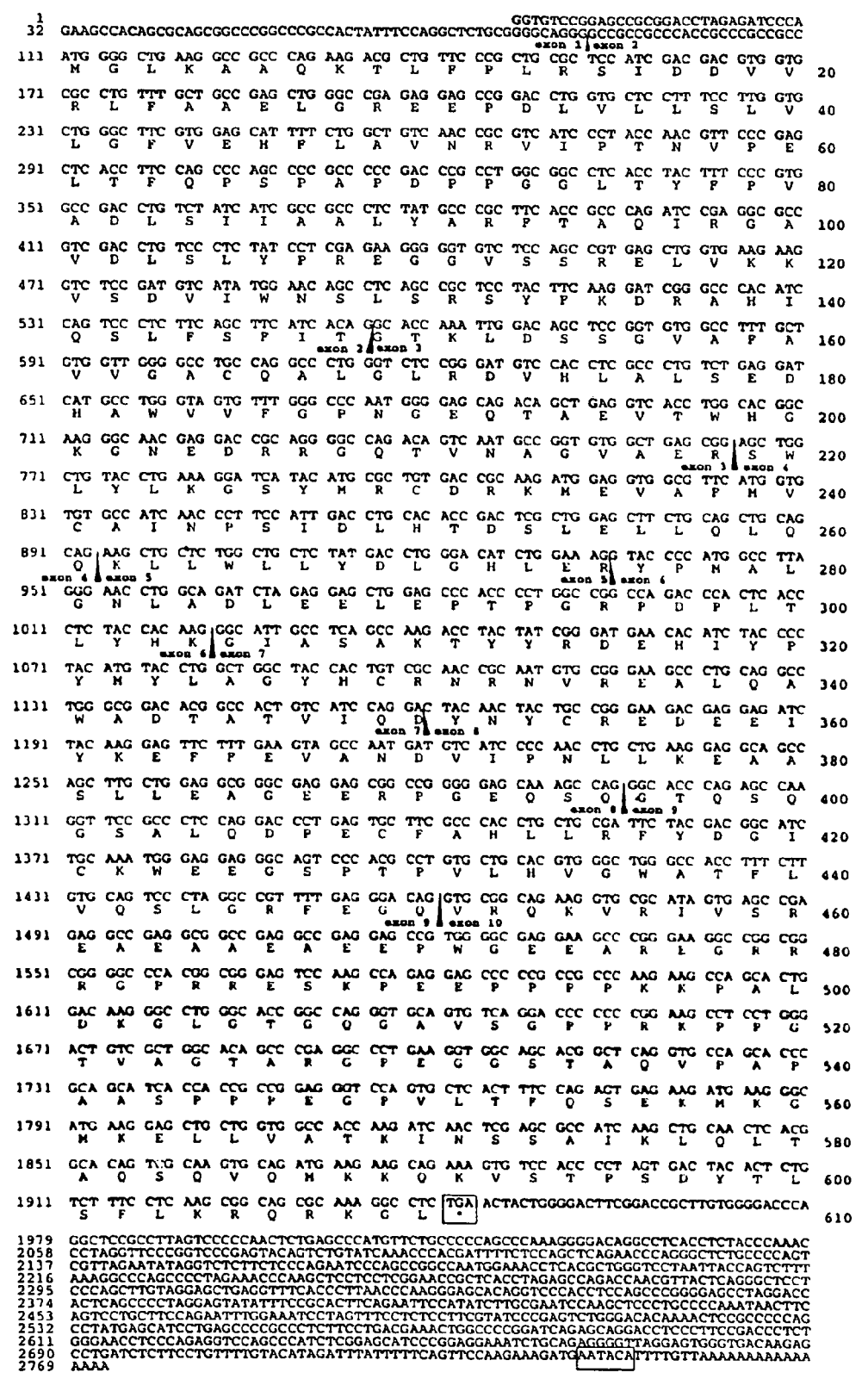

This invention provides for methods of genotyping family members in which relatives are diagnosed with multiple endocrine neoplasias type 1. Conventional methods of genotyping are provided herein. In one embodiment, genomic analysis is preferred, where mutations in MEN1 are determined using primers and probes which bind to either the exons or introns of MEN1 gene. A map of the MEN1 gene is provided in FIG. 1.

A variety of methods of specific DNA and RNA measurement using nucleic acid hybridization techniques are known to those of skill in the art. See Sambrook. For example, one method for evaluating the presence or absence of MEN1 DNA in a sample involves a Southern transfer. Briefly, the digested genomic DNA is run on agarose slab gels in buffer and transferred to membranes. Hybridization is carried out using the probes discussed above. Visualization of the hybridized portions allows the qualitative determination of the presence, alteration or absence of MEN1.

Similarly, a Northern transfer may be used for the detection of menin mRNA in samples of RNA from cells expressing MEN1. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the MEN1 transcript.

The selection of a nucleic acid hybridization format is not critical. A variety of nucleic acid hybridization formats are known to those skilled in the art. For example, common formats include sandwich assays and competition or displacement assays. Hybridization techniques are generally described in "*Nucleic Acid Hybridization, A Practical Approach*," Ed. Hames, B. D. and Higgins, S. J., IRL Press, 1985; Gall and Pardue (1969), *Proc. Natl. Acad. Sci.*, U.S.A., 63:378-383; and John, Burnsteil and Jones (1969) *Nature*, 223:582-587. For example, sandwich assays are commercially useful hybridization assays for detecting or isolating nucleic acid sequences. Such assays utilize a "capture" nucleic acid covalently immobilized to a solid support and labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

It will be appreciated that nucleic acid hybridization assays can also be performed in an array-based format as described in Fodor et al. (1991) Science, 251: 767-777; Sheldon et al. (1993) Clinical Chemistry 39(4): 718-719, and Kozal et al. (1996) Nature Medicine 2(7): 753-759. In this approach, arrays bearing a multiplicity of different "probe" nucleic acids (usually amplified DNA) are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see, e.g., Jackson et al. (1996) Nature Biotechnology, 14 1685-1691, and Chee et al. (1995) Science, 274: 610-613).

The nucleic acid sequences used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may act as a negative probe in an assay sample where only the mutant MEN1 is present.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P. H., Eds., Elsevier (1985), pp. 9-20.)

The sensitivity of the hybridization assays may be enhanced through use of a nucleic acid amplification system which multiples the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

A preferred embodiment is the use of wild-type specific or allele-specific amplifications. In the case of PCR, the amplification primers are designed to bind to a portion of the MEN1 gene but the terminal base at the 3' end is used to discriminate between the mutant or wild-type forms of MEN1. If the terminal base matches the point mutation or the wild-type, polymerase dependent three primer (3'-) extension can proceed and an amplification product is detected. This method for detecting point mutations or polymorphisms is described in detail by Sommer (1989) *Mayo Clin. Proc.* 64:1361-1372. By using appropriate controls, one can develop a kit having both positive and negative amplification products. The products can be detected using specific probes or by simply detecting their presence or absence. A variation of the PCR method uses LCR where the point of discrimination, i.e., either the point mutation or the wild-type bases fall between the LCR oligonucleotides. The ligation of the oligonucleotides becomes the means for discriminating between the mutant and wild-type forms of MEN1.

An alternative means for determining the level of expression of MEN1 is in situ hybridization. In situ hybridization assays are well known and are generally described, e.g., in Angerer (1987) *Methods Enzymol.* 152:649-660. In an in situ hybridization assay cells, preferentially bovine lymphocytes are fixed to a solid support, typically a glass slide. If DNA is to be probed, the cells are denatured with heat or alkali. The cells are then contacted with a hybridization solution at a moderate temperature to permit annealing of MEN1 specific probes that are labelled. The probes are preferably labelled with radioisotopes or fluorescent reporters.

Immunological Detection of Menin

In addition to the detection of MENI or MEN1 gene expression (message) using nucleic acid hybridization technology (including amplification techniques), one can also use immunoassays to detect menin polypeptide. Because menin is associated with diseases of the endocrine tissue, the determination of the presence of wild type or mutated menin is preferably performed on tissue biopsies from these organs. Immunoassays can be used to qualitatively or quantitatively analyze menin. A general overview of the applicable technology can be found in, e.g., Harlow and Lane, *Antibodies: A Laboratory Manual*, Cold Spring Harbor Pubs., N.Y. (1988).

A. Antibodies to Menin

Methods of producing polyclonal and monoclonal antibodies that react specifically with menin are known to those of skill in the art. See, e.g., Coligan (1991), CURRENT PROTOCOLS IN IMMUNOLOGY, Wiley/Greene, NY: and Harlow and Lane; Stites et al. (eds.) BASIC AND CLINICAL IMMUNOLOGY (4th ed.) Lange Medical Publications, Los Altos, Calif., and reference cited therein; Goding (1986), MONOCLONAL ANTIBODIES: PRINCIPLES AND PRACTICE (2d ed.) Academic Press, New York, N.Y.; and Kohler and Milstein (1975), *Nature* 256:495-497. Such techniques include antibody preparation by selection of antibodies from libraries of recombinant antibodies in phage or similar vectors. See, Huse et al. (1989), *Science,* 246: 1275-1281; and Ward et al. (1989) *Nature,* 341:544-546. For example, in order to produce antisera for use in an immunoassay, the menin or a antigenic fragment thereof, is isolated as described herein. For example, recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used an immunogen.

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-menin proteins, between different wild-type menin allelic variation, or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

In producing antibodies specifically or selectively reactive with menin, a specific wild-type polymorphic variant of menin (encoded by an MEN1 allele), or a mutated menin (the mutation typically resulting in loss of biologic activity), a recombinant protein or synthetic peptide are the preferred immunogens for the production of monoclonal or polyclonal antibodies. Naturally occurring protein may also be used either in pure or impure form. Synthetic peptides are made using the protein sequences described herein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animals's immune response to the immunogen preparation is monitored by taking test bleeds and determining the titer of reactivity to menin. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. In one exemplary method, spleen cells from an animal immunized with a desired antigen are immortalized, commonly by fusion with a myeloma cell (See, e.g., Kohler and Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275-1281. Such techniques also include selection of antibodies from libraries of recombinant antibodies displayed in phage ("phage display libraries") or similar on cells. See, also Ward (1989) *Nature* 341:544, Hoogenboom (1997) *Trends Biotechnol.* 15:62-70; Katz (1997) *Annu. Rev. Biophys. Biomol. Struct.* 26:27-45. Recombinant antibodies can be expressed by transient or stable expression vectors in mammalian cells, as in Norderhaug (1997) *J. Immunol. Methods* 204:77-87; on yeast cells, as in Boder (1997) *Nat. Biotechnol.* 15:553-557.

Once menin specific antibodies are available, menin can be measured by a variety of immunoassay methods with qualitative and quantitative results available to the clinician. For a review of immunological and immunoassay procedures in general, see *Basic and Clinical Immunology* 7th Edition (D. Stites and A. Terr ed.) 1991. Moreover, the immunoassays of the present invention can be performed in any of several configurations, which are reviewed extensively in *Enzyme Immunoassay,* E. T. Maggio, ed., CRC Press, Boca Raton, Fla. (1980); "Practice and Theory of Enzyme Immunoassays," Tijssen; and, Harlow and Lane.

Immunoassays to measure menin in a human sample may use a polyclonal antiserum which was raised to the protein completely or partially encoded by SEQ ID NO:2, or a fragment thereof. This antiserum can be selected to have low crossreactivity against non-menin proteins, or, low crossreactivity with different wild-type polymorphic variants of menin (encoded by MEN1 alleles), or, low crossreactivity with any menin form other than that used to immunize, i.e., if a menin mutant polypeptide is the immunogen, low crossreactivity towards any other form of menin. Any such crossreactivity can be removed by immunoabsorption prior to use in the immunoassay.

In order to produce antisera for use in an immunoassay, menin or a fragment thereof, is isolated as described herein. For example, recombinant protein is produced in a transformed cell line. An inbred strain of mice such as Balb/c is immunized with the protein or a peptide using a standard adjuvant, such as Freund's adjuvant, and a standard mouse immunization protocol. Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-menin proteins, using a competitive binding immunoassay such as the one described in Harlow and Lane, supra, at pages 570-573 and below.

B. Immunological Binding Assays

As explained above, menin expression is associated with a normal cell phenotype and mutations that result in the under expression of menin of inability to express a functional, wild-type menin are indicative of either the existence or the likelihood of multiple endocrine neoplasia type 1. In a preferred embodiment, menin is detected and/or quantified using any of a number of well recognized immunological binding assays (see, e.g., U.S. Pat. Nos. 4,366,241; 4,376, 110; 4,517,288; and 4,837,168). For a review of the general immunoassays, see also *Methods in Cell Biology Volume* 37: *Antibodies in Cell Biology,* Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case the menin or antigenic subsequence thereof). The capture agent is a moiety that specifically binds to the analyte. In a preferred embodiment, the capture agent is an antibody that specifically binds menin (or to a specific allelic or mutant form). The antibody (anti-menin) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled menin polypeptide or a labeled anti-menin antibody. Alternatively, the labeling agent may be a third moiety, such as another antibody, that specifically binds to the antibody/menin complex. In a preferred embodiment, the labeling agent is a second menin bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin. Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401-1406, and Akerstrom, et al. (1985) *J. Immunol.,* 135: 2589-2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting menin in biological or tissue samples may be either competitive or noncompetitive. Non-competitive immunoassays are assays in which the amount of captured analyte (in this case the protein) is directly measured. In one preferred "sandwich" assay, for example, the capture agent (anti-menin antibodies) can be bound directly to a solid substrate where they are immobilized. These immobilized antibodies then capture menin present in the test sample. Menin is thus immobilized is then bound by a labeling agent, such as a second menin antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of menin (analyte) present in the sample is measured indirectly by measuring the amount of an added (exogenous) analyte (i.e., the menin) displaced (or competed away) from a capture agent (anti-menin antibody) by the analyte present in the sample. In one competitive assay, a known amount of, in this case, the menin is added to the sample and the sample is then contacted with a capture agent, in this case an antibody that specifically binds to the menin. The amount of menin bound to the antibody is inversely proportional to the concentration of menin present in the sample. In a particularly preferred embodiment, the antibody is immobilized on a solid substrate. The amount of the menin bound to the antibody may be determined either by measuring the amount of menin present in an menin/antibody complex, or alternatively by measuring the amount of remaining uncomplexed protein. The amount of menin may be detected by providing a labeled menin molecule.

A hapten inhibition assay is another preferred competitive assay. In this assay a known analyte, in this case the menin is immobilized on a solid substrate. A known amount of anti-menin antibody is added to the sample, and the sample is then contacted with the immobilized menin. In this case, the amount of anti-menin antibody bound to the immobilized menin is inversely proportional to the amount of menin present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, the partially encoded by SEQ ID NO:2 can be immobilized to a solid support. Proteins are added to the assay which compete with the binding of the antisera to the immobilized antigen. The ability of the above proteins to compete with the binding of the antisera to the immobilized protein is compared to the menin of SEQ ID NO:2. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the considered proteins, e.g., distantly related homologues.

The immunoabsorbed and pooled antisera are then used in a competitive binding immunoassay as described above to compare a second protein, thought to be perhaps the protein of this invention, as a wild-type polymorphic variant of menin, to the immunogen protein (i.e. menin of SEQ ID NO:2, or, a polypeptide encoded by SEQ ID NO:1). In order to make this comparison, the two proteins are each assayed at a wide range of concentrations and the amount of each protein required to inhibit 50% of the binding of the antisera to the immobilized protein is determined. If the amount of the second protein required is less than 10 times the amount of immunogen that is required (to inhibit 50% of the binding of the antisera), then the second protein is said to specifically bind to an antibody generated to the immunogen.

3. Other Assay Formats

In a particularly preferred embodiment, Western blot (immunoblot) analysis is used to detect and quantify the presence of menin in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the menin. The anti-menin antibodies specifically bind to the menin peptides on the solid support. These antibodies may be directly labeled or alternatively may be subsequently detected using labeled antibodies (e.g., labeled sheep anti-mouse antibodies) that specifically bind to the anti-menin antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Reduction of Non-Specific Binding

One of skill in the art will appreciate that it is often desirable to use non-specific binding in immunoassays. Particularly, where the assay involves an antigen or antibody immobilized on a solid substrate it is desirable to minimize the amount of non-specific binding to the substrate. Means of using such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

5. Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used: thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatase, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter of photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Gene Therapy Applications

A variety of human diseases may be treated by therapeutic approaches that involve stably introducing a gene into a human cell such that the gene may be transcribed and the gene product may be produced in the cell. Diseases amenable to treatment by this approach include inherited diseases, particularly those diseases such as MEN1, where the defect is with a single gene, MEN1. For discussions on the application of gene therapy towards the treatment of genetic as well as acquired diseases See Miller, A. D. (1992) *Nature* 357:455-460, and Mulligan, R. C. (1993) *Science* 260:926-932. For a review of gene therapy procedures, see, e.g., Zhang (1996) *Cancer Metastasis Rev.* 15:385-401; Anderson, *Science* (1992) 256: 808-813; Nabel (1993) *TIBTECH* 11: 211-217; Mitani (1993) *TIBTECH* 11: 162-166; Mulligan (1993) *Science,* 926-932; Dillon (1993) *TIBTECH* 11: 167-175; Miller (1992) *Nature* 357: 455-460; Van Brunt (1988) *Biotechnology* 6(10): 1149-1154; Vigne (1995) Restorative Neurology and Neuroscience 8: 35-36, Kremer (1995) *British Medical Bulletin* 51(1) 31-44; Haddada (1995) in *Current Topics in Microbiology and Immunology,* Doerfler and Böhm (eds) Springer-Verlag, Heidelberg Germany; and Yu (1994) *Gene Therapy,* 1:13-26.

The vectors useful in the practice of the present invention are typically derived from viral genomes. Vectors which may be employed include recombinantly modified enveloped or non-enveloped DNA and RNA viruses, preferably selected from baculoviridiae, parvoviridiae, picornoviridiae, herpesveridiae, poxviridae, adenoviridiae, or picornnaviridiae. Chimeric vectors may also be employed which exploit advantageous aspects of each of the parent vector properties, see e.g., Feng (1997) *Nature Biotechnology* 15:866-870. Such viral genomes may be modified by recombinant DNA techniques to include the tumor suppressor gene and may be engineered to be replication deficient, conditionally replicating or replication competent. In the preferred practice of the invention, the vectors are replication deficient or conditionally replicating. Preferred vectors are derived from the adenoviral, adeno-associated viral and retroviral genomes.

Conditionally replicating viral vectors are used to achieve selective expression in particular cell types while avoiding untoward broad spectrum infection. Examples of conditionally replicating vectors are described, e.g., in Bischoff (1996) *Science* 274:373-376; Pennisi (1996) *Science* 274: 342-343; Russell (1994) *Eur. J. of Cancer* 30A(8):1165-1171. Additionally, the viral genome may be modified to include inducible promoters which achieve replication or expression of the transgene only under certain conditions. Examples of inducible promoters are known in the scientific literature (See, e.g. Yoshida (1997) *Biochem. Biophys. Res. Comm.* 230:426-430; Iida (1996) *J. Virol.* 70(9):6054-6059; Hwang (1997) *J. Virol* 71(9): 7128-7131; Lee (1997) *Mol. Cell. Biol.* 17:5097-5105; Dreher (1997) *J. Biol. Chem.* 272; 29364-29371. The transgene may also be under control of a tissue specific promoter region allowing expression of the transgene only in particular cell types.

Retroviral Vectors

Retroviral vectors have the ability to stably integrate the transferred gene sequences into the chromosomal DNA of the target cell. Retroviral vectors are particularly attractive because they are very efficient in stably transducing a high percentage of target cells. Accordingly most of the approved gene therapy clinical protocols use retroviral vectors. See Miller, A. D., (1992) supra. Retroviral vectors are particularly useful for modifying cells because of the high efficiency with which the retroviral vectors transduce target cells and integrate into the target cell genome. Additionally, the retroviruses harboring the retroviral vector are capable of infecting cells from a wide variety of tissues.

Retroviral vectors are produced by genetically manipulating retroviruses. Retroviruses are called RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C., In: *Experimental Manipulation of Gene Expression,* M. Inouye (ed), 155-173 (1983); Mann, R., et al., *Cell,* 33:153-159 (1983), Cone, R. D. and R. C. Mulligan, *Proceedings of the National Academy of Sciences, U.S.A.,* 81:6349-6353 (1984).

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, *Biotechniques* 4:504-512 (1986), Mann, et al., *Cell* 33:153-159 (1983), Cone and Mulligan, *Proc. Natl. Acad. Sci. USA* 81:6349-6353 (1984), Eglitis, M. A, et al., (1988) *Biotechniques* 6:608-614, Miller, A. D. et al. (1989) *Biotechniques* 7:981-990, Miller, A. D. (1992) *Nature,* supra, Mulligan, R. C. (1993), supra, and Gould, B. et al., and International Patent Application No. WO 92/07943 entitled "Retroviral Vectors Useful in Gene Therapy".

The retroviral vector particles are prepared by recombinantly inserting the wild type MEN1 into a retrovirus vector and packaging the vector with retroviral capsid proteins by use of a packaging cell line. The resultant retroviral vector particle is incapable of replication in the host cell and is capable of integrating into the host cell genome as a proviral sequence containing the MEN1. As a result, the patient is capable of producing menin and thus restore the cells to a normal, non-cancerous phenotype.

Packaging cell lines are used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13. See Miller et al., *J. Virol.* 65:2220-2224 (1991). Examples of other packaging cell lines are described in Cone, R. and Mulligan, R. C., *Proceedings of the National Academy of Sciences, USA,* 81:6349-6353 (1984) and in Danos, O. and R. C. Mulligan, *Proceedings of the National Academy of Sciences, USA,* 85: 6460-6464 (1988), Eglitis, M. A., et al. (1988) supra and Miller, A. D., (1990) supra. Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

Adeno-Associated Virus (AAV)-Based Vectors

Adeno-associated virus (AAV)-based vectors are also used to transduce cells with target nucleic acids, e.g., in the in vitro production of nucleic acids and peptides, and in in vivo and ex vivo gene therapy procedures. See, Okada (1996) *Gene Ther.* 3:957-964; West (1987) *Virology* 160:38-47; Carter (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351, for an overview of AAV vectors. Construction of recombinant AAV vectors are described in a number of publications, including Lebkowski, U.S. Pat. No. 5,173,414, Tratschin (1985) *Mol. Cell. Biol.* 5(11):3251-3260; Tratschin (1984) *Mol. Cell. Biol.* 4: 2072-2081; Hermonat (1984) *Proc. Natl. Acad. Sci. USA* 81: 6466-6470; McLaughlin (1988) and Samulski (1989) *J. Virol.* 63:03822-3828. Cell lines that can be transformed by rAAV include those described in Lebkowski (1988) *Mol. Cell. Biol.,* 8:3988-3996.

Adenoviral Vectors

The invention also provides for in vivo expression of menin-encoding nucleic acid in an adenoviral vector suitable for gene therapy. Human clinical studies have demonstrated that adenovirus vectors are effective means to infect tumors and express transgene and viral products by tumor cells, resulting in a significant anti-tumor immune response (see, e.g., Gahery-Segard (1997) J. Clin. Invest. 100:2218-2226). The use of adenoviral vectors in vivo, and for gene therapy, is well described in the patent and scientific literature, e.g., see, Horellou (1997) *Mol. Neurobiol.* 15: 241-256; Hermens (1997) *J. Neurosci. Methods., Jan.,* 71(1): 85-98; Zeiger (1996) *Surgery* 120:921-925; Channon (1996) *Cardiovasc Res.* 32:962-972; Huang (1996) *Gene Ther.* 3:980-987; Zepeda (1996) *Gene Ther.* 3:973-979; Yang (1996) *Hum. Mol. Genet.* 5:1703-1712; Caruso (1996) *Proc. Natl. Acad. Sci. USA* 93:11302-11306; Rothmann (1996) *Gene Ther.* 3:919-926; Haecker (1996) *Hum. Gene Ther.* 7:1907-1914. The use of adenoviral vectors is described in detail in WO 96/25507. Adenovirus type 5 and adenovirus type 2 genomes are described, e.g., by Chroboczek (1992) *Virology* 186:280-285. Adenovirus vectors for gene therapy are typically made replication defective by deletion of adenovirus early ("E") region 1 ("E1") region genes.

For isolation, propagation, and large-scale production of such vectors, E1 functions are supplied in trans from a stable cell line. Typically, adenovirus vectors used for clinical studies are produced in the 293 cell, a human embryonic kidney cell line expressing E1 functions from an integrated segment of the left end of the adenovirus (Ad) type 5 (Ad5) genome (see, e.g., Hehir (1996) *J. Virol.* 70:8459-8467) (other cell lines can be used to the propagation of early region 1-deleted adenoviral vectors, e.g., the human embryonic retinoblast (HER) line 911, with a plasmid containing base pairs 79-5789 of the Ad5 genome, see Fallaux (1996) *Hum. Gene Ther.* 7:215-222). Many adenoviral vectors are engineered such that the inserted gene of interest (e.g., a transgene, the wild type menin) replaces the adenovirus E1a, E1b, and E3 genes; subsequently the replication-defective vector can be propagated only in human 293 cells that supply the deleted E1 gene functions in trans. Alternatively, adenoviral E1, E3, and E2b gene functions are deleted (see, e.g., Amalfitano (1998) *J. Virol.* 72:926-933), or, the E1 and/or E4 genes are deleted (see, e.g., Brough (1996) *J. Virol.* 70:6497-6501; Armentano (1995) *Hum. Gene Ther.* 6:1343-1353). Adenoviral vectors can also contain a deletion in the adenovirus early region 3 and/or early region 4.

Alternatively, to achieve amplification of recombinant replication defective adenoviral transgene expression in vivo, a the trans complementation approach can be used, where cotransduction of an E1-defective adenovirus with a plasmid containing the deleted E1 functions into cells results in E1-defective virus production by those cells (see, e.g., Dion (1996) *Cancer Gene Ther.* 3:230-237, Goldsmith (1994) *Hum. Gene Ther.* 5:1341-134). Adenoviral vectors can include a deletion of some or all of the protein IX gene (four trimers of Ad protein IX are embedded in the upper surface of viral hexons to create a highly-stable assembly, see, e.g., Babiss (1991) *J. Virol.* 65:598-605; Furcinitti (1989) *EMBO J.* 8:3563-3570) (for Ad pIX deletion vectors, see, e.g., Krougliak (1995) *Hum. Gene Ther.* 6:1575-1586). In one embodiment, the adenoviral vectors include deletions of the E1a and/or E1b sequences.

The following examples provide by way of illustration only and not by way of limitation. Those of skill will readily recognize a variety of noncritical parameters which could be changed or modified to yield essentially similar results.

EXAMPLES

Example 1

Identification of MEN1 Mutations

The following example details the characterization and definition of a number of MEN1 mutations Using the above methods, it was possible to define a number of MEN1 mutations. The invention provides for the discovery that mutations in MEN1 were responsible for multiple endocrine neoplasia type 1 (MEN1), and that some non-hereditary (i.e., somatic or acquired) mutations in both alleles of MEN1 can be responsible for many different endocrine tumors.

Patients clinically diagnosed as having multiple endocrine neoplasia type 1 (MEN1) were selected for the study. One population studied came from 15 typical multiple endocrine neoplasia type 1 affected families. The diagnosis of MEN1 was based upon presence of tumors in two of the three principal systems (parathyroid, enteropancreatic endocrine tissue, anterior pituitary). Diagnosis of familial MEN1 required at least one first-degree relative with a tumor of one or more of these systems. There were 1 to 47 living affected members in each kindred, with a median of 5. All participating family members gave full informed consent in a protocol approved by the NIDDK Institutional Review Board.

Genomic DNA was isolated from blood samples using the Qiagen Kit (Chatsworth, Calif.). Exons 2-10 of MEN1 were amplified individually or in groups from genomic DNA using primers designed from intron sequences. The relevant PCR primers and ddF primer sequences can be found in Table 1. PCR was performed in 25 µl reactions containing 100 ng DNA, 0.2 µM of each primer, 200 µM dNTPs, 10 mM Tris-HCl pH 8.3, 50 mM KCl, 1.5 mM MgCl2, 0.001% (w/v) gelatin, and 0.5U AmpliTaq Gold (Perkin Elmer, Branchburg, N.J.). Thermal cycling in a Perkin Elmer System 9600 was performed at 92° C. for 10 minutes and then 35 cycles of 94° C. for 30 sec, 60° C. for 30 sec, 72° C. for 1-2 min, followed by a final extension at 72° C. for 5 min. DMSO at a final concentration of 5% was included for exons 2, 9 and 10.

After checking for purity of the PCR product by electrophoresing 5 µl on agarose, dideoxy fingerprinting (ddF) was carried out as described by Sarkar (1992) *Genomics* 13:441, with modifications. The primary PCR products were subjected to a dideoxy chain termination reaction using ddGTP (Boehringer Mannheim, Indianapolis, Ind.) in a 10 µl reaction containing 1 µl primary PCR template (20 ng), 0.15 µM end-labeled ddF primer (using gamma-$^{33}$P ATP from Dupont-NEN, Boston, Mass. and T4 polynucleotide kinase from Promega, Madison, Wis.), 25 µM dNTPs, 200 µM ddGTP, 10 mM Tris-HCl pH 8.3, 50 mM KCl, 1.5 mM MgCl2, 0.001% (w/v) gelatin, and 1 U Amplitaq Gold. Reactions were cycled in a Perkin Elmer System 9600: 92° C. for 10 min to activate Taq Gold and then 35 cycles of 94° C. for 30 seconds, 65° C. for 30 seconds and 72° C. for 1 minute; after a final extension step at 72° C. for 5 minutes the reactions were held at 4° C. To the 10 µl ddF reactions was added 40 µl of buffer containing 7M urea, 50% formamide, bromophenol blue and xylene cyanol. Reactions were heated at 94° C. for 5 minutes and chilled in ice, 5 µl was loaded on a non-denaturing gel (0.75×MDE, FMC Bioproducts, Rockland, Me.) in 0.5×TBE) on a sequencing apparatus. The gel was electrophoresed at a constant power of 8 Watts at room temperature in a buffer system consisting of 0.5×TBE in the top reservoir and 0.8×TBE with 0.5M sodium acetate in the bottom reservoir, until the bromophenol blue reached the bottom of the gel. The gel was removed on Whatman paper and dried for 30 minutes in a sequencing gel drier and autoradiographed overnight.

One ddF primer could screen about 250 bp region; if the region to be screened in the primary PCR product was larger, additional primers were used for ddF. Samples showing changes in band patterns were subjected to cycle sequencing using the same primary PCR product and the same end-labeled primer as was used in the ddF reaction. For insertion or deletion type changes in which the actual bases involved could not be ascertained from the sequence of the heterozygous patient sample, the primary PCR product was cloned in the TA cloning vector pCRII (Invitrogen, San Diego, Calif.) and then sequenced.

Confirmation that the mutation segregated with MEN1 was achieved by direct sequencing of PCR products from other affected family members. Independent confirmation of the sequence change in affected individuals was achieved by restriction digestion of the appropriate exon PCR product for 512delC (creates an AflII site), W436R (creates MspI and NciI sites), and R527X (creates a Bsu36I site). For the remainder, analysis was carried out with radiolabeled allele-specific 16 to 20-mers corresponding to the wild type or mutant sequence, hybridized to slot blots of exon PCR products, as described by Lyons (1990) Science 249:655).

For example, FIG. 2 shows the detection of frameshift and nonsense MEN1 mutations. Analysis of exon 2 in an MEN1 patient and a normal control, using dideoxy fingerprinting (ddF), revealed pattern differences (arrows, FIG. 2A) indicative of a MEN1 mutation. Abnormal ddF pattern in exon 9 from a different patient is shown in FIG. 2B. Identification of a single nucleotide deletion by sequencing of a cloned exon 2 PCR product from the patient whose ddF pattern is shown in FIG. 2A is shown in FIG. 2C. The sequence shown is of the antisense strand; the mutation is 512delC. This frameshift mutation was confirmed by detecting the presence of a new AflII site in PCR-amplified exon 2 from this patient and two affected relatives (FIG. 2D). Direct sequencing of the exon 9 PCR product from panel (B), revealed the presence of a heterozygous C to T (C=>T) substitution (FIG. 2D). Again the sequence is of the antisense strand; the mutation creates a stop codon: TGG to TAG or W436X (TGG=>TAG or W436X) (abbreviations indicating mutations follow standard nomenclature, see Beaudet (1993) supra).

Figure 3:
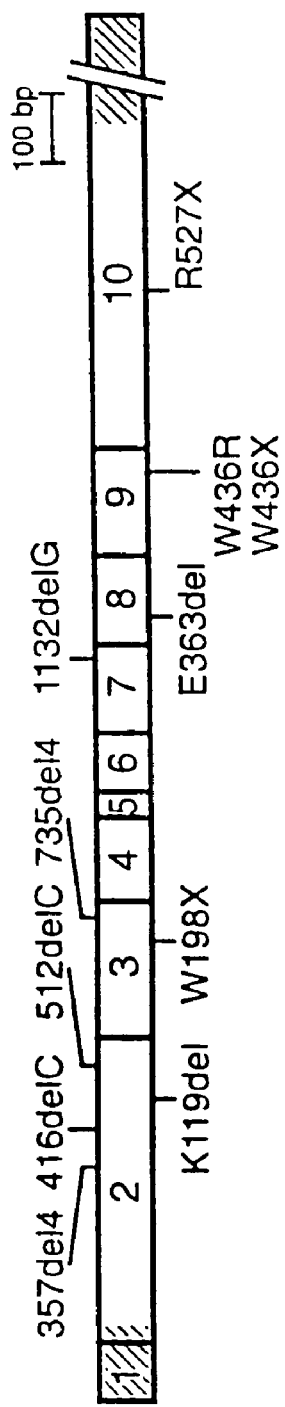
FIG. 3 show a summary of mutations identified in 15 unrelated MEN1 patients. The locations of the five frameshift mutations are shown above a diagram of the MEN1 gene, with the exons numbered; crosshatched areas are untranslated. Two in-frame deletions of a single amino acid, three nonsense mutations, and one missense mutation (W436R) are shown below the gene diagram. The 416delC and 512delC mutations were each encountered twice. Mutation abbreviations follow standard nomenclature, e.g., as described by Beaudet (1993) "A suggested nomenclature for designating mutations," *Hum Mutat.* 2(4):245-248.

FIG. 3 show a summary of mutations identified in 15 unrelated MEN1 patients. The locations of the five frameshift mutations are shown above a diagram of the MEN1 gene, with the exons numbered, crosshatched areas are untranslated. Two in-frame deletions of a single amino acid, three nonsense mutations, and one missense mutation (W436R) are shown below the gene diagram. The 416delC and 512delC mutations were each encountered twice.

FIG. 4 shows a summary of mutations identified in unrelated MEN1 patients using similar techniques (abbreviations indicating MEN1 mutations follow standard nomenclature, see Beaudet (1993) supra).

Two examples of abnormal ddF patterns are shown in FIGS. 2A (exon 2) and 3B (exon 9). Sequencing of PCR-amplified material (FIG. 2E), or in some instances cloned products (FIG. 2C), was used to identify the nature of the abnormality. For nine different mutations where other affected family members were available for study (all except E363del and W436X), confirmation that the observed alteration was inherited concordantly with the MEN1 phenotype was carried out (FIG. 2D). A total of 5 frameshift mutations, 3 nonsense mutations, 2 in-frame deletions, and one missense alteration were identified (FIG. 3). Two mutations (416delC and 512delC) were encountered twice in families not known to be related. The missense mutation (W436R) was not observed in an analysis of 71 normal DNA samples. Three relatively common polymorphisms, L432L (CTG/CTA), D418D (GAC/GAT) and A541T (GCA/ACA) were also encountered, and were observed in 0.7%, 42% and 4% of normal chromosomes respectively (n=142).

The identification of significant mutations in 13 of 15 unrelated affected individuals establishes that the gene responsible for multiple endocrine neoplasia type 1 (MEN1) has been identified. The observation that many of the mutations detected (FIG. 3) would most likely result in loss of function of the protein product is consistent with a tumor suppressor mechanism, and distinguishes MEN1 from the related disorder multiple endocrine neoplasia type 2.

Example 2

Expression of Recombinant Human MEN1 Gene Product

The following example details the expression, isolation and characterization of recombinant human menin. The example also illustrates the production of antiserum to human menin polypeptide and its use in the characterization of menin using Western blots.

The insect expression system for the production of human menin utilizes *Drosophila* Schneider 2 cells (Schneider (1972) *J. Embryol. Exp. Morph.* 27:363-365) transfected with an appropriate vector containing the menin cDNA of the invention. The pMT/V5-His vector was used, it contains an inducible metallothionein promoter for regulated transcription of insert (i.e., menin) RNA (Johansen (1989) supra). pMT/V5-His also contains a sequence encoding six histidines linked to the carboxy terminus of menin in order to facilitate purification of the menin protein. Restriction sites were added to the menin cDNA using PCR prior to facilitate its insertion into the appropriate site in pMT/V5-His. S2 cells were stably transfected with the pMT/V5-His menin vector. The selection plasmid, pCoHYGRO (van der Straten (1989) supra) was co-transfected into S2 cells to produce stable cells under the antibiotic selection of hygromycin-B. S2 cells were grown at 23° C. in DES Expression Medium supplemented with 2 mM L-glutamine.

To characterize and isolate the recombinantly expressed human menin polypeptide, the cells were harvested and lysed in a buffer containing 50 mM Tris HCl (pH 7.8), 150 mM NaCl and 1% Nonidet P-40 (Invitrogen Corp., Carlsbad, Calif.).

The molecular weight of menin from was measured by SDS-PAGE under reduced conditions followed by Western blot analysis of the gel. Antiserum specific for human menin was generated by injecting a menin peptide corresponding to amino acids numbered 583 to 610 into rabbits; and purified as described by Goldsmith (1987) *J. Biol. Chem.* 262:14683-14688. Western blot analysis with anti-menin peptide antiserum demonstrated that the recombinant menin had an apparent molecular weight of 68,000 daltons.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated MEN1 gene, wherein said MEN1 gene encodes a protein having the amino acid sequence of SEQ ID NO:2.

2. An isolated nucleic acid comprising SEQ ID NO:1.

3. The isolated MEN1 gene of claim 1, wherein the MEN1 gene comprises SEQ ID NO:3.

4. A kit for detecting in a test sample the presence or absence of a mutation in a MEN1 gene having the sequence of SEQ ID NO:3, the kit comprising:
   an oligonucleotide competent to discriminate between the wildtype gene and a mutant form, wherein the oligonucleotide discriminates between the wildtype gene and mutant form in exons 2, 3, 4, 5, 6, 7, 8, 9, and/or 10 of SEQ ID NO:3; and a reagent for detecting and discrimination.

5. The kit of claim 4, further comprising amplification primer pairs for specifically amplifying exons 2 through 10 of MEN1, SEQ ID NO:3, either individually or in groups.

6. An isolated cell transfected with a nucleic acid comprising the nucleic acid of claim 1.

7. The isolated cell of claim 6, wherein the transfected nucleic acid comprises SEQ ID NO:3.

8. The isolated cell of claim 6, wherein the cell is a human cell.

9. An expression cassette comprising the nucleic acid of claim 1, wherein the nucleic acid is operably linked to a promoter.

10. The expression cassette of claim 9, further comprising an expression vector.

11. A method for detecting the presence or absence of a mutation in a target region in exon 2, 3, 4, 5, 6, 7, 8, 9, and/or 10 of SEQ ID NO:3 in a nucleic acid sample, the method comprising:
   contacting the nucleic acid sample with an oligonucleotide corresponding to the wildtype SEQ ID NO:3, wherein the oligonucleotide discriminates between the wildtype gene and mutant form in exons 2, 3, 4, 5, 6, 7, 8, 9, and/or 10 of SEQ ID NO:3;
   contacting a normal control sample comprising the wildtype exons 2, 3, 4, 5, 6, 7, 8, 9, and/or 10 of SEQ ID NO:3 with said oligonucleotide; and
   comparing the formation of a duplex in the nucleic acid sample between said oligonucleotide and said target region in exon 2, 3, 4, 5, 6, 7, 8, 9, and/or 10 of SEQ ID NO:3 to the formation of a duplex in the normal control sample between said oligonucleotide and said target region in exon 2, 3, 4, 5, 6, 7, 8, 9 and/or 10 of SEQ ID NO: 3; wherein the presence of the duplex in the nucleic acid sample is indicative of the wildtype target region and the absence of the duplex is indicative of a mutation in the wildtype target region.

12. A method for detecting the presence or absence of a mutation in a target region in exon 2, 3, 4, 5, 6, 7, 8, 9, and/or 10 of SEQ ID NO:3 in a nucleic acid sample, the method comprising:
   amplifying the target region in exon 2, 3, 4, 5, 6, 7, 8, 9 and/or 10 of SEQ ID NO:3 in the nucleic acid sample and the target region in exon 2, 3, 4, 5, 6, 7, 8, 9 and/or 10 of SEQ ID NO:3 in a normal control sample comprising the wildtype exons 2, 3, 4, 5, 6, 7, 8, 9, and/or 10 of SEQ ID NO:3 with primer pairs specifically amplifying exons 2, 3, 4, 5, 6, 7, 8, 9, and/or 10 of SEQ ID NO:3, either individually or in groups;
   contacting amplified product from the nucleic acid sample with an oligonucleotide corresponding to the wildtype SEQ ID NO:3, wherein the oligonucleotide discriminates between the wildtype gene and mutant form in exons 2, 3, 4, 5, 6, 7, 8, 9, and/or 10 of SEQ ID NO:3;
   contacting amplified product from the normal control sample with said oligonucleotide; and comparing the formation of a duplex in the nucleic acid sample between said oligonucleotide and said target region in exon 2, 3, 4, 5, 6, 7, 8, 9, and/or 10 of SEQ ID NO:3 to the formation of a duplex in the normal control sample between said oligonucleotide and said target region in exons 2, 3, 4, 5, 6, 7, 8, 9 and/or 10 of SEQ ID NO: 3; wherein the presence of the duplex is indicative of the wildtype target region and the absence of the duplex is indicative of a mutation in the wildtype target region.

13. A method for detecting the presence of a mutation in a target region in exon 2, 3, 4, 5, 6, 7, 8, 9, and/or 10 of SEQ ID NO:3 in a nucleic acid sample, the method comprising:

incubating the nucleic acid sample in an amplification reaction comprising primer pairs for specifically amplifying exons 2 through 10 of MEN1, SEQ ID NO:3 either individually or in groups; and determining the sequence of the target region, wherein a change in sequence in comparison to SEQ ID NO:3 is indicative of the presence of a mutation.

14. An isolated cell comprising the nucleic acid of claim 2.

15. The isolated cell of claim 14, wherein the cell is a human cell.

16. An expression cassette comprising the nucleic acid of claim 2, wherein the nucleic acid is operably linked to a promoter.

17. The expression cassette of claim 16, further comprising an expression vector.

* * * * *

```
                          SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
         (A) LENGTH: 2772 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 111..1940
         (D) OTHER INFORMATION: /product= "human menin"

(ix) FEATURE:
         (A) NAME/KEY: exon
         (B) LOCATION: 1..87

(ix) FEATURE:
         (A) NAME/KEY: exon
         (B) LOCATION: 88..555

(ix) FEATURE:
         (A) NAME/KEY: exon
         (B) LOCATION: 556..764

(ix) FEATURE:
         (A) NAME/KEY: exon
         (B) LOCATION: 765..893

(ix) FEATURE:
         (A) NAME/KEY: exon
         (B) LOCATION: 894..934
```

```
    (ix) FEATURE:
         (A) NAME/KEY: exon
         (B) LOCATION: 935..1022

(ix) FEATURE:
         (A) NAME/KEY: exon
         (B) LOCATION: 1023..1159

(ix) FEATURE:
         (A) NAME/KEY: exon
         (B) LOCATION: 1160..1295

(ix) FEATURE:
         (A) NAME/KEY: exon
         (B) LOCATION: 1296..1460

(ix) FEATURE:
         (A) NAME/KEY: exon
         (B) LOCATION: 1461..2764

(xi) SEQUENCE DESCRIPTION: SEQ ID NO: 1:

GGTGTCCGGA GCCGCGGACC TAGAGATCCC AGAAGCCACA GCGCAGCGGC CCGGCCCGCC        60

ACTATTTCCA GGCTCTGCGG GGCAGGGGCC GCCGCCCACC GCCCGCCGCC ATG GGG         116
                                                        Met Gly
                                                          1

CTG AAG GCC GCC CAG AAG ACG CTG TTC CCG CTG CGC TCC ATC GAC GAC        164
Leu Lys Ala Ala Gln Lys Thr Leu Phe Pro Leu Arg Ser Ile Asp Asp
        5                  10                  15

GTG GTG CGC CTG TTT GCT GCC GAG CTG GGC CGA GAG GAG CCG GAC CTG        212
Val Val Arg Leu Phe Ala Ala Glu Leu Gly Arg Glu Glu Pro Asp Leu
 20                  25                  30

GTG CTC CTT TCC TTG GTG CTG GGC TTC GTG GAG CAT TTT CTG GCT GTC        260
Val Leu Leu Ser Leu Val Leu Gly Phe Val Glu His Phe Leu Ala Val
 35                  40                  45                  50

AAC CGC GTC ATC CCT ACC AAC GTT CCC GAG CTC ACC TTC CAG CCC AGC        308
Asn Arg Val Ile Pro Thr Asn Val Pro Glu Leu Thr Phe Gln Pro Ser
                 55                  60                  65

CCC GCC CCC GAC CCG CCT GGC GGC CTC ACC TAC TTT CCC GTG GCC GAC        356
Pro Ala Pro Asp Pro Pro Gly Gly Leu Thr Tyr Phe Pro Val Ala Asp
                 70                  75                  80

CTG TCT ATC ATC GCC GCC CTC TAT GCC CGC TTC ACC GCC CAG ATC CGA        404
Leu Ser Ile Ile Ala Ala Leu Tyr Ala Arg Phe Thr Ala Gln Ile Arg
         85                  90                  95

GGC GCC GTC GAC CTG TCC CTC TAT CCT CGA GAA GGG GGT GTC TCC AGC        452
Gly Ala Val Asp Leu Ser Leu Tyr Pro Arg Glu Gly Gly Val Ser Ser
100                 105                 110

CGT GAG CTG GTG AAG AAG GTC TCC GAT GTC ATA TGG AAC AGC CTC AGC        500
Arg Glu Leu Val Lys Lys Val Ser Asp Val Ile Trp Asn Ser Leu Ser
115                 120                 125                 130

CGC TCC TAC TTC AAG GAT CGG GCC CAC ATC CAG TCC CTC TTC AGC TTC        548
Arg Ser Tyr Phe Lys Asp Arg Ala His Ile Gln Ser Leu Phe Ser Phe
                135                 140                 145

ATC ACA GGC ACC AAA TTG GAC AGC TCC GGT GTG GCC TTT GCT GTG GTT        596
Ile Thr Gly Thr Lys Leu Asp Ser Ser Gly Val Ala Phe Ala Val Val
                150                 155                 160

GGG GCC TGC CAG GCC CTG GGT CTC CGG GAT GTC CAC CTC GCC CTG TCT        644
Gly Ala Cys Gln Ala Leu Gly Leu Arg Asp Val His Leu Ala Leu Ser
        165                 170                 175

GAG GAT CAT GCC TGG GTA GTG TTT GGG CCC AAT GGG GAG CAG ACA GCT        692
Glu Asp His Ala Trp Val Val Phe Gly Pro Asn Gly Glu Gln Thr Ala
        180                 185                 190

GAG GTC ACC TGG CAC GGC AAG GGC AAC GAG GAC CGC AGG GGC CAG ACA        740
Glu Val Thr Trp His Gly Lys Gly Asn Glu Asp Arg Arg Gly Gln Thr
195                 200                 205                 210
```

-continued

```
GTC AAT GCC GGT GTG GCT GAG CGG AGC TGG CTG TAC CTG AAA GGA TCA      788
Val Asn Ala Gly Val Ala Glu Arg Ser Trp Leu Tyr Leu Lys Gly Ser
            215                 220                 225

TAC ATG CGC TGT GAC CGC AAG ATG GAG GTG GCG TTC ATG GTG TGT GCC      836
Tyr Met Arg Cys Asp Arg Lys Met Glu Val Ala Phe Met Val Cys Ala
        230                 235                 240

ATC AAC CCT TCC ATT GAC CTG CAC ACC GAC TCG CTG GAG CTT CTG CAG      884
Ile Asn Pro Ser Ile Asp Leu His Thr Asp Ser Leu Glu Leu Leu Gln
    245                 250                 255

CTG CAG CAG AAG CTG CTC TGG CTG CTC TAT GAC CTG GGA CAT CTG GAA      932
Leu Gln Gln Lys Leu Leu Trp Leu Leu Tyr Asp Leu Gly His Leu Glu
260                 265                 270

AGG TAC CCC ATG GCC TTA GGG AAC CTG GCA GAT CTA GAG GAG CTG GAG      980
Arg Tyr Pro Met Ala Leu Gly Asn Leu Ala Asp Leu Glu Glu Leu Glu
275                 280                 285                 290

CCC ACC CCT GGC CGG CCA GAC CCA CTC ACC CTC TAC CAC AAG GGC ATT     1028
Pro Thr Pro Gly Arg Pro Asp Pro Leu Thr Leu Tyr His Lys Gly Ile
                295                 300                 305

GCC TCA GCC AAG ACC TAC TAT CGG GAT GAA CAC ATC TAC CCC TAC ATG     1076
Ala Ser Ala Lys Thr Tyr Tyr Arg Asp Glu His Ile Tyr Pro Tyr Met
            310                 315                 320

TAC CTG GCT GGC TAC CAC TGT CGC AAC CGC AAT GTG CGG GAA GCC CTG     1124
Tyr Leu Ala Gly Tyr His Cys Arg Asn Arg Asn Val Arg Glu Ala Leu
        325                 330                 335

CAG GCC TGG GCG GAC ACG GCC ACT GTC ATC CAG GAC TAC AAC TAC TGC     1172
Gln Ala Trp Ala Asp Thr Ala Thr Val Ile Gln Asp Tyr Asn Tyr Cys
    340                 345                 350

CGG GAA GAC GAG GAG ATC TAC AAG GAG TTC TTT GAA GTA GCC AAT GAT     1220
Arg Glu Asp Glu Glu Ile Tyr Lys Glu Phe Phe Glu Val Ala Asn Asp
355                 360                 365                 370

GTC ATC CCC AAC CTG CTG AAG GAG GCA GCC AGC TTG CTG GAG GCG GGC     1268
Val Ile Pro Asn Leu Leu Lys Glu Ala Ala Ser Leu Leu Glu Ala Gly
                375                 380                 385

GAG GAG CGG CCG GGG GAG CAA AGC CAG GGC ACC CAG AGC CAA GGT TCC     1316
Glu Glu Arg Pro Gly Glu Gln Ser Gln Gly Thr Gln Ser Gln Gly Ser
            390                 395                 400

GCC CTC CAG GAC CCT GAG TGC TTC GCC CAC CTG CTG CGA TTC TAC GAC     1364
Ala Leu Gln Asp Pro Glu Cys Phe Ala His Leu Leu Arg Phe Tyr Asp
        405                 410                 415

GGC ATC TGC AAA TGG GAG GAG GGC AGT CCC ACG CCT GTG CTG CAC GTG     1412
Gly Ile Cys Lys Trp Glu Glu Gly Ser Pro Thr Pro Val Leu His Val
    420                 425                 430

GGC TGG GCC ACC TTT CTT GTG CAG TCC CTA GGC CGT TTT GAG GGA CAG     1460
Gly Trp Ala Thr Phe Leu Val Gln Ser Leu Gly Arg Phe Glu Gly Gln
435                 440                 445                 450

GTG CGG CAG AAG GTG CGC ATA GTG AGC CGA GAG GCC GAG GCG GCC GAG     1508
Val Arg Gln Lys Val Arg Ile Val Ser Arg Glu Ala Glu Ala Ala Glu
                455                 460                 465

GCC GAG GAG CCG TGG GGC GAG GAA GCC CGG GAA GGC CGG CGG CGG GGC     1556
Ala Glu Glu Pro Trp Gly Glu Glu Ala Arg Glu Gly Arg Arg Arg Gly
            470                 475                 480

CCA CGG CGG GAG TCC AAG CCA GAG GAG CCC CCG CCG CCC AAG AAG CCA     1604
Pro Arg Arg Glu Ser Lys Pro Glu Glu Pro Pro Pro Pro Lys Lys Pro
        485                 490                 495

GCA CTG GAC AAG GGC CTG GGC ACC GGC CAG GGT GCA GTG TCA GGA CCC     1652
Ala Leu Asp Lys Gly Leu Gly Thr Gly Gln Gly Ala Val Ser Gly Pro
    500                 505                 510

CCC CGG AAG CCT CCT GGG ACT GTC GCT GGC ACA GCC CGA GGC CCT GAA     1700
Pro Arg Lys Pro Pro Gly Thr Val Ala Gly Thr Ala Arg Gly Pro Glu
```

```
                515                 520                 525                 530
GGT GGC AGC ACG GCT CAG GTG CCA GCA CCC GCA GCA TCA CCA CCG CCG                  1748
Gly Gly Ser Thr Ala Gln Val Pro Ala Pro Ala Ala Ser Pro Pro Pro
                    535                 540                 545

GAG GGT CCA GTG CTC ACT TTC CAG AGT GAG AAG ATG AAG GGC ATG AAG                  1796
Glu Gly Pro Val Leu Thr Phe Gln Ser Glu Lys Met Lys Gly Met Lys
            550                 555                 560

GAG CTG CTG GTG GCC ACC AAG ATC AAC TCG AGC GCC ATC AAG CTG CAA                  1844
Glu Leu Leu Val Ala Thr Lys Ile Asn Ser Ser Ala Ile Lys Leu Gln
        565                 570                 575

CTC ACG GCA CAG TCG CAA GTG CAG ATG AAG AAG CAG AAA GTG TCC ACC                  1892
Leu Thr Ala Gln Ser Gln Val Gln Met Lys Lys Gln Lys Val Ser Thr
    580                 585                 590

CCT AGT GAC TAC ACT CTG TCT TTC CTC AAG CGG CAG CGC AAA GGC CTC                  1940
Pro Ser Asp Tyr Thr Leu Ser Phe Leu Lys Arg Gln Arg Lys Gly Leu
595                 600                 605                 610

TGAACTACTG GGGACTTCGG ACCGCTTGTG GGGACCCAGG CTCCGCCTTA GTCCCCAAC                 2000

TCTGAGCCCA TGTTCTGCCC CCAGCCCAAA GGGGACAGGC CTCACCTCTA CCCAAACCCT                2060

AGGTTCCCGG TCCCGAGTAC AGTCTGTATC AAACCCACGA TTTTCTCCAG CTCAGAACCC                2120

AGGGCTCTGC CCCAGTCGTT AGAATATAGG TCTCTTCTCC CAGAATCCCA GCCGGCCAAT                2180

GGAAACCTCA CGCTGGGTCC TAATTACCAG TCTTTAAAGG CCCAGCCCCT AGAAACCCAA                2240

GCTCCTCCTC GGAACCGCTC ACCTAGAGCC AGACCAACGT TACTCAGGGC TCCTCCCAGC                2300

TTGTAGGAGC TGAGGTTTCA CCCTTAACCC AAGGGAGCAC AGGTCCCACC TCCAGCCCGG                2360

GGAGCCTAGG ACCACTCAGC CCCTAGGAGT ATATTTCCGC ACTTCAGAAT TCCATATCTT                2420

GCGAATCCAA GCTCCCTGCC CCAAATAACT TCAGTCCTGC TTCCAGAATT TGGAAATCCT                2480

AGTTTCCTCT CCTTCGTATC CCGAGTCTGG GACACAAAAC TCCGCCCCCA GCCTATGAGC                2540

ATCCTGAGCC CCGCCCTCTT CCTGACGAAA CTGGCCCCGG ATCAGAGCAG GACCTCCCTT                2600

CCGACCCTCT GGGAACCTCC CAGAGGTCCA GCCCATCTCG GAGCATCCCG GAGGAAATCT                2660

GCAGAGGGGT TAGGAGTGGG TGACAAGAGC CTGATCTCTT CCTGTTTTGT ACATAGATTT                2720

ATTTTTCAGT TCCAAGAAAG ATGAATACAT TTTGTTAAAA AAAAAAAAA AA                        2772

(2) INFORMATION FOR SEQ ID NO: 2:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
                20                  25                  30

Asp Leu Val Leu Leu Ser Leu Val Leu Gly Phe Val Glu His Phe Leu
            35                  40                  45

Ala Val Asn Arg Val Ile Pro Thr Asn Val Pro Glu Leu Thr Phe Gln
        50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95
```

```
Ile Arg Gly Ala Val Asp Leu Ser Leu Tyr Pro Arg Glu Gly Val
            100                 105                 110
Ser Ser Arg Glu Leu Val Lys Lys Val Ser Asp Val Ile Trp Asn Ser
        115                 120                 125
Leu Ser Arg Ser Tyr Phe Lys Asp Arg Ala His Ile Gln Ser Leu Phe
    130                 135                 140
Ser Phe Ile Thr Gly Thr Lys Leu Asp Ser Ser Gly Val Ala Phe Ala
145                 150                 155                 160
Val Val Gly Ala Cys Gln Ala Leu Gly Leu Arg Asp Val His Leu Ala
            165                 170                 175
Leu Ser Glu Asp His Ala Trp Val Val Phe Gly Pro Asn Gly Glu Gln
        180                 185                 190
Thr Ala Glu Val Thr Trp His Gly Lys Gly Asn Glu Asp Arg Arg Gly
    195                 200                 205
Gln Thr Val Asn Ala Gly Val Ala Glu Arg Ser Trp Leu Tyr Leu Lys
        210                 215                 220
Gly Ser Tyr Met Arg Cys Asp Arg Lys Met Glu Val Ala Phe Met Val
225                 230                 235                 240
Cys Ala Ile Asn Pro Ser Ile Asp Leu His Thr Asp Ser Leu Glu Leu
            245                 250                 255
Leu Gln Leu Gln Gln Lys Leu Leu Trp Leu Leu Tyr Asp Leu Gly His
        260                 265                 270
Leu Glu Arg Tyr Pro Met Ala Leu Gly Asn Leu Ala Asp Leu Glu Glu
    275                 280                 285
Leu Glu Pro Thr Pro Gly Arg Pro Asp Pro Leu Thr Leu Tyr His Lys
        290                 295                 300
Gly Ile Ala Ser Ala Lys Thr Tyr Tyr Arg Asp Glu His Ile Tyr Pro
305                 310                 315                 320
Tyr Met Tyr Leu Ala Gly Tyr His Cys Arg Asn Arg Asn Val Arg Glu
            325                 330                 335
Ala Leu Gln Ala Trp Ala Asp Thr Ala Thr Val Ile Gln Asp Tyr Asn
        340                 345                 350
Tyr Cys Arg Glu Asp Glu Glu Ile Tyr Lys Glu Phe Phe Glu Val Ala
    355                 360                 365
Asn Asp Val Ile Pro Asn Leu Leu Lys Glu Ala Ser Leu Leu Glu
        370                 375                 380
Ala Gly Glu Glu Arg Pro Gly Glu Gln Ser Gln Gly Thr Gln Ser Gln
385                 390                 395                 400
Gly Ser Ala Leu Gln Asp Pro Glu Cys Phe Ala His Leu Leu Arg Phe
            405                 410                 415
Tyr Asp Gly Ile Cys Lys Trp Glu Glu Gly Ser Pro Thr Pro Val Leu
        420                 425                 430
His Val Gly Trp Ala Thr Phe Leu Val Gln Ser Leu Gly Arg Phe Glu
    435                 440                 445
Gly Gln Val Arg Gln Lys Val Arg Ile Val Ser Arg Glu Ala Glu Ala
        450                 455                 460
Ala Glu Ala Glu Glu Pro Trp Gly Glu Glu Ala Arg Glu Gly Arg Arg
465                 470                 475                 480
Arg Gly Pro Arg Arg Glu Ser Lys Pro Glu Glu Pro Pro Pro Lys
            485                 490                 495
Lys Pro Ala Leu Asp Lys Gly Leu Gly Thr Gly Gln Gly Ala Val Ser
        500                 505                 510
```

```
Gly Pro Pro Arg Lys Pro Pro Gly Thr Val Ala Gly Thr Ala Arg Gly
            515                 520                 525

Pro Glu Gly Gly Ser Thr Ala Gln Val Pro Ala Pro Ala Ala Ser Pro
530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
            565                 570                 575

Leu Gln Leu Thr Ala Gln Ser Gln Val Gln Met Lys Lys Gln Lys Val
            580                 585                 590

Ser Thr Pro Ser Asp Tyr Thr Leu Ser Phe Leu Lys Arg Gln Arg Lys
            595                 600                 605

Gly Leu
    610

(2) INFORMATION FOR SEQ ID NO: 3:

(i) SEQUENCE CHARACTERISTICS:
        (A) LENGTH: 9180 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..9180
        (D) OTHER INFORMATION: /note= "genomic sequence for MEN1 gene"

(ix) FEATURE:
        (A) NAME/KEY: exon
        (B) LOCATION: 1680..1766

(ix) FEATURE:
        (A) NAME/KEY: intron
        (B) LOCATION: 1767..2264

(ix) FEATURE:
        (A) NAME/KEY: exon
        (B) LOCATION: 2265..2732

(ix) FEATURE:
        (A) NAME/KEY: intron
        (B) LOCATION: 2733..4296

(ix) FEATURE:
        (A) NAME/KEY: exon
        (B) LOCATION: 4297..4505

(ix) FEATURE:
        (A) NAME/KEY: intron
        (B) LOCATION: 4506..4715

(ix) FEATURE:
        (A) NAME/KEY: exon
        (B) LOCATION: 4716..4844

(ix) FEATURE:
        (A) NAME/KEY: intron
        (B) LOCATION: 4845..5176

(ix) FEATURE:
        (A) NAME/KEY: exon
        (B) LOCATION: 5177..5217

(ix) FEATURE:
        (A) NAME/KEY: intron
        (B) LOCATION: 5218..5297

(ix) FEATURE:
        (A) NAME/KEY: exon
```

```
        (B) LOCATION: 5298..5385

(ix) FEATURE:
    (A) NAME/KEY: intron
    (B) LOCATION: 5386..6024

(ix) FEATURE:
    (A) NAME/KEY: exon
    (B) LOCATION: 6025..6161

(ix) FEATURE:
    (A) NAME/KEY: intron
    (B) LOCATION: 6162..6622

(ix) FEATURE:
    (A) NAME/KEY: exon
    (B) LOCATION: 6623..6758

(ix) FEATURE:
    (A) NAME/KEY: intron
    (B) LOCATION: 6759..7195

(ix) FEATURE:
    (A) NAME/KEY: exon
    (B) LOCATION: 7196..7360

(ix) FEATURE:
    (A) NAME/KEY: intron
    (B) LOCATION: 7361..7577

(ix) FEATURE:
    (A) NAME/KEY: exon
    (B) LOCATION: 7578..8881

(xi) SEQUENCE DESCRIPTION: SEQ ID NO: 3:

CTGGTCTTGA ACTCCTGGCC TCAAGCAATC CTCCTGCTTC AGCTTCCCAA AGTGTTGTAA      60

TTACAGGCAT GAGCCTGGCA TGAACTTGAC ACTATTGAGA TATACTGGTC AGGTATTTTG     120

TGGAATGTCC CTCAACTCTG TTTTGCCAGA TGTTTTCTCA TGATTAGAGG AGAGTTATAA     180

ATTTTGAGGA AAATCCAGAG AGGTGAAGAG GTGAAGTAGG GCAGAAATTT AATCTGTTTT     240

ATTTACTGCT ATATACCGAG TGTCTGGAAC TTGGCCCATG GTAAGTACCA AAAATCTGTT     300

TTTTTTGAAT GAATAAGCAA ATAAATGAGT GACCGTGGAA ATTTAGTATT ATTTCAAAGT     360

TTCAAAGCGT TGTTGATACA GGCCAGGCAC AGTGGCTCAC ACCTGTAATC CCAGCACTTT     420

TGGAGGCCGA GGTAGGAGGA TCACTTGAGG TCAGGAGTTC GAGACCAGCC TGACCAACAT     480

GGTGACACCC CTGTCTCTAC TAAGTAAAAT ACAAAAATTA GCCAAGTGTG GTGGCAGGCA     540

CCTGTAATCC CGGCTACTTG GGAAGCTGAG GCAGAAGAAT CACTTGAACC TGGGAGGCAG     600

AGGTTGCAGT GAGCCGAGAT CACCCCACTG CACTCCAGCC TGAGTGACAG AGCGAGACTC     660

TGTCTCAAAA CAAATAAACA AATAACTACT CTTTGGCCGG GTAAGGTGGT TCACGCCTGT     720

AATTTTAGCA CTTTGGGAGG CTGAGGCGGG CAGATCACTT GAGGTTAGGG GTTCGAGACC     780

AGTCTGGCCA ACATGGTGAA ACCCCATCTC TACTTAAAAT ACAAAAGTT TTCTGGGTGT      840

GGTGGCGGAC GCCTATAATC CCAGCTACTT GGGACTTTTT TTTAAGACGG AATCTCACTC     900

TGTTGCCCAG GCTGGAGTGC AGTGGCAAGA TTCTGGCTCA CTGAAGCCTC CGCCTCCCAG     960

GTTCAAGGGG ATTCCCCGCG CCTCAGCCTC CCAAGTAGCT GGGAATCCCT GTCTCTGCAA    1020

AAAAAAAAAA AAAAAAAAAC AAAAAATATA TATATATATA TATATGTGTG TGTGTGTGTG    1080

TGTGTGTGTG TTATATGTAT ATATATTTAT GTATATGCAC ATACACACAA AATTAGGCGG    1140

GAGTGGTGGC GCACGCCTGT GATCACAGCT ACTCGGGAGG CTGAGGCACG AGAATCGCTT    1200

GAGCCCGTGA AGTCGAGGCT GCAGTGAGCC CAGATCGAGC CACTGCATTC CAGCCTGGGC    1260

GAAAGAGAAA GACCGTGTCT CAAAACAAAC AAACAAAAGC TACTCTTAGC ACGTGTTAGA    1320
```

-continued

```
GTATCTCGCG GGCGGAAGTG GGAAACGAGT GCTGCACACA GAGTAGGCAT CTTTATATGT    1380

TAACAGACAC TGATACCCAG CTAAAGCGGC TGAACACATT TACTCTCTGG CAGTGTTTAA    1440

AAGTATCTGT TTTTCTCATA TTGTTTTATT TTAATTTTTT CTGGATCAAG CAACCTGATC    1500

TTTTTCCTCA TAACTTGCCG ACCGACCCGT GACAGCAAAA CCGGCAGAAG CTCGGCGACC    1560

TCCCACCCCG AGTCTGCAGG TAGTGCCCCC GGACTACATT TTCCAGAAGG CACTGCGGGC    1620

ACGCTTCCTG CCTGGTCGGC CTGAAGGGAA GGGCCAATCC CTGAGTATCT CGGGAAGGAG    1680

GTGTCCGGAG CCGCGGACCT AGAGATCCCA GAAGCCACAG CGCAGCGGCC CGGCCCGCCA    1740

CTATTTCCAG GCTCTGCGGG GCAGGGGTGG GCCCAGACTC CACTTCCCGG CGGGTAGTGC    1800

GACCCTAGGG GCGGGACTTC ATGTCCCAGC AGGCTCCGGG CGGCGTGCGC CGCGGTGCCT    1860

AGTGTGGGAT GTAAGCGCGG AGGTGGGCGA GGGGGACCGA GGCCAGGACT CTCCTTGGGG    1920

TTTGGGGGCT TGACCTGGGT GCGCTTTCTG GACAGACTTT ACAGCCCCCG GGGCACAGT     1980

CGTAGAGAGG GGGCGGGGCG GCCATTGGGG CTCCTCATTG GGGTGCTTGG GGCGCACCCC    2040

ATCGGGTACC GGGCGTCCCG GAATTGTGGG GGACAAAAAG GCTCTGCAGT CTCGGCTGAG    2100

GGGTCTCACC GACAAAAGAG GGGAAGCCGG TGAGCAGAGG CTGAAGAGGG TGGGGAAGCA    2160

GGGGAGCTGT GCGTGTGTCG GGGCGGGTGG AACCTTAGCG GACCCTGGGA GGAGGCTCCC    2220

CGGCCGAACC TGCCCGACCC TCCCTCCCCC GGCTTGCCTT GCAGGCCGCC GCCCACCGCC    2280

CGCCGCCATG GGGCTGAAGG CCGCCCAGAA GACGCTGTTC CCGCTGCGCT CCATCGACGA    2340

CGTGGTGCGC CTGTTTGCTG CCGAGCTGGG CCGAGAGGAG CCGGACCTGG TGCTCCTTTC    2400

CTTGGTGCTG GGCTTCGTGG AGCATTTTCT GGCTGTCAAC CGCGTCATCC CTACCAACGT    2460

TCCCGAGCTC ACCTTCCAGC CCAGCCCCGC CCCCGACCCG CCTGGCGGCC TCACCTACTT    2520

TCCCGTGGCC GACCTGTCTA TCATCGCCGC CCTCTATGCC CGCTTCACCG CCCAGATCCG    2580

AGGCGCCGTC GACCTGTCCC TCTATCCTCG AGAAGGGGGT GTCTCCAGCC GTGAGCTGGT    2640

GAAGAAGGTC TCCGATGTCA TATGGAACAG CCTCAGCCGC TCCTACTTCA AGGATCGGGC    2700

CCACATCCAG TCCCTCTTCA GCTTCATCAC AGGTTGGAGC CCAGTAGGTG GGAATCTTAT    2760

CCATGACCCA CTTCTTCAAA ACCCTCCATG GTTTACAGAA CCCTTTTAAG AACTGTAAGC    2820

CTTGTGAGGT TCGGCAGGTG TTATTTTCCT CTTTGCAGTT GGGAAACTGA AGCCCAGAGA    2880

GGGGAAATGA TATGCCAAAG TCACACACGG CATGGCAGGG CTGGAAGTGA AGCCTGATCA    2940

CTTGGCTCCA AATCATCAAC CTCACCTCTG CCCCCTCAGC ACCCCACCC  TTGCCACTGA    3000

ACAGCTACAG GAGTTCTAAG CATGAGACAC AGAGGGCGGC AGCAGATTTA GGGGGCAAGA    3060

AGATGAAATT GGGCTGCATT TGAGGCAGTT AAACAAAATA ATGGCTATGA AGATTTTTTT    3120

TTTTTTTTTT TTTTGAGACA GGGTCTCACT CTGTCCCCCA GGCTGGAGTG CAGTGGTGTG    3180

ATCATGGCTC ACTGCAGCCT CAGTCTCCCT GGGCTCAGAG ATCCTCCAAC CTCAGCCTCC    3240

TGAGTAGCTG AGAGTACAGG CATGCACCGT GGTGCTGGTT AATTTTTTGT ATTTTTTTG    3300

TAGAGATGGT GTCTCACTAT GTGGCCCAGA CTGGTCTTGA ACTCTTGGGC TCAAGTGATC    3360

TGCCCGCCTC AGTCTCCCAA ATGCTGGGAT TACAGGTGTG AGCCACCGCA ACTGGTGGCC    3420

TATGAAAATT TTTTTTTTTT TTCAGACGGC GTCTCACTCT GTCGCCCAGG CTGGAGTGCA    3480

GTGGTGCAAT CTCGGCTCAC TGCAAGCTCT GCCTCCTGCT TTCATGCCAT TCTCCTGCCT    3540

CCTGCCTCAG CCTCCTGAGT AGCTGGGACT ACAGGAGCCT GCCACCATGC CTGGCTAATT    3600

TTTTTTTGGA TTTTTAGTAG AGACGAGGTT TCACCATGTT AGCCAGGATG GTCTCGATCT    3660
```

| | |
|---|---|
| CCTGACCTCG TGATCCGCCC GCCTTGGCCT CCCAAAGTGC TGGGATTACA GGCGTGAGCC | 3720 |
| ACCGCACCTG GTCAAAAATG TTTGAGACAG AGAAGGGGCT TGACCTCAAA AGGCTTAAGA | 3780 |
| GTCAGGGCTT GCAAAGAGCT TTGCACCAAG CCCGGTTGAC TGGCAATCCC ATCCTGGTGT | 3840 |
| GCCATATTGA GAAGGAATCA GAGGCTGCTT CTCAGCTTAG CAGGAAAAGA GTGCAGAGAT | 3900 |
| AAATGAGGGT TATTTGTTGG TGGGTGTATA GCCAGAGAGT GTTGGCCAGC GTCCTGTTTT | 3960 |
| TGCCATTCCT GTTTTAACCT AGTAAGTGCA GTAAAATGGA ATCCCTAAAT CCATAGAATA | 4020 |
| TATAATAGAG TTGCAGAGAA AGACGAGGTA GGGCCAAAGG CTGGGTCAGC TACAGGATAT | 4080 |
| CCAGAAAGGT ATCTTGTTGG ACATAGAGGG TGTAAACAGG GAGAGAGTCT TTGAACACGT | 4140 |
| GGGAGGGAAG GGATGGAGGG ATAGTGGGCA GGAGAATCTG AGGTTGGGTC ACAGGCTTGG | 4200 |
| AAAGGGAGTG GGAGGGAGTG TGGCCCATCA CTACCTGGCC CCTTTCCCCA TGTTAAAGCA | 4260 |
| CAGAGGACCC TCTTTCATTA CCTCCCCCTT CCACAGGCAC CAAATTGGAC AGCTCCGGTG | 4320 |
| TGGCCTTTGC TGTGGTTGGG GCCTGCCAGG CCCTGGGTCT CCGGGATGTC CACCTCGCCC | 4380 |
| TGTCTGAGGA TCATGCCTGG GTAGTGTTTG GGCCCAATGG GGAGCAGACA GCTGAGGTCA | 4440 |
| CCTGGCACGG CAAGGGCAAC GAGGACCGCA GGGGCCAGAC AGTCAATGCC GGTGTGGCTG | 4500 |
| AGCGGGTATT GTTCCCTCCC CCCAGCCTTG TCCCCTTCAT ACTGTAGTAG CCCAAGCCAC | 4560 |
| CCAAGGGACT CCATTTTCTT GGGCCACACC CCTTTCTTCC CATCACCACC CACATAGGAA | 4620 |
| GGGAAGACAG AAGAGCCCCT TTTCCTGGCT GTCATTCCCT GAAGCAGGCA CAGGGTGGGC | 4680 |
| CATCATGAGA CATAATGATC TCATCCCCCC CTAAGAGCTG GCTGTACCTG AAAGGATCAT | 4740 |
| ACATGCGCTG TGACCGCAAG ATGGAGGTGG CGTTCATGGT GTGTGCCATC AACCCTTCCA | 4800 |
| TTGACCTGCA CACCGACTCG CTGGAGCTTC TGCAGCTGCA GCAGGTGAGG GCTGAGCCAA | 4860 |
| TGGGGCAGGA CTGGGCTAGG CCAGACTTGA CTTGCTGTGG GACCCTGGGC AGGGGCACTT | 4920 |
| TCCCTTCCTG AGCTTCAGCT TCCCCTCCTG GAAAAATGGG TTAGTAATTC CTGGCCTGGC | 4980 |
| CTTTCCCAGG GCTCTTGGGA GAGTAGAATT GAGATGTGAA ATTGCTTTGA CTCCATTAAA | 5040 |
| GGGCTGGTCC CAGAATTTTG GCCCTTCCAC ATGGTGGGTG GTCCCTGTTG GTTCTGACCC | 5100 |
| CCACCTCTGC CCGATAGGCT AAGGACCCGT TCTCCTCCCT GTTCCGTGGC TCATAACTCT | 5160 |
| CTCCTTCGGC TCCTAGAAGC TGCTCTGGCT GCTCTATGAC CTGGGACATC TGGAAAGGTC | 5220 |
| AGTAGAGGGA AGTGGCCAGG CTGCGCCTGG TGAGGCCGGG GGGCTGGGTG GCAGCCTGAA | 5280 |
| TTATGATCCT TTCCTAGGTA CCCCATGGCC TTAGGGAACC TGGCAGATCT AGAGGAGCTG | 5340 |
| GAGCCCACCC CTGGCCGGCC AGACCCACTC ACCCTCTACC ACAAGGTGGG GGCATCTAAG | 5400 |
| GAGGGTGCAG AAGGGAGACC CTAACAGTGG CTGAGGCAGG GGCCCTCATC TGGGCAGATG | 5460 |
| AGAAGAGAAC TTTGTGTGTT GGGGGGTATC GCCCATCCAG TCTCACTTTG TGTCAACTGT | 5520 |
| GTGCAGAATC AGTTCAGTCA GGGCTGTCTG AGGGGTGTCC AGGGTTCCCC AGCCTGGGAG | 5580 |
| TGGCAGGGGC TGCATTTGTC CCCTCAGCCC TGCCTTTTCT GCCACTGCTT ACTGTCCTTC | 5640 |
| CTGGAGTATA ACAGAGGTCA AATGTGGTAG GAGCACTGAA GAGGGGGTGT TCACTTGGTG | 5700 |
| GGTGTAGGTG GGGAGGAGGG CCATTGGGCT GGGCTTGAAA GTCTTTGGTG ATGTGTAGAA | 5760 |
| GAGTGTCTGA GAAAGAGAAG GGCCCTGAGC TCGGAGGGCA GGCCCACCC CTGCAGTCTG | 5820 |
| CCCCAGGCCT CAGCCAGCAG TCCTGTAGAC CCAGGGAGGA GACCAGGTAG AAGGGCTGGC | 5880 |
| AGCGAGTGGA GGTGGGAGTG GAGATGGAGA GGACTCCCTG GGATCTTCCT GTGGCCCTT | 5940 |
| CTGGGTGTGC CCTGGTGGGG CATTTGTGCC AGCAGGGCAG CTGGGGCTGC CTCCCTGAGG | 6000 |
| ATCCTCTGCC TCACCTCCAT CCAGGGCATT GCCTCAGCCA AGACCTACTA TCGGGATGAA | 6060 |

```
CACATCTACC CCTACATGTA CCTGGCTGGC TACCACTGTC GCAACCGCAA TGTGCGGGAA    6120

GCCCTGCAGG CCTGGGCGGA CACGGCCACT GTCATCCAGG AGTGAGGATC CCCCTACTAG    6180

GGCCTGCAGC CTGTCCTTTC TTCCCCTCCA TCAGTTTCCA ACCACCCTCG TCCAGGACTG    6240

AGGCCTGGCT CCCACGCCCC ATCCCCTTTC CATCCAGTCC CTAGGCAGCA AGGCCACCAT    6300

TACCCAGGAG GTAGGGACCC TGATTAAGGT GTCACATCTT TCCCTCCCTC CCCTCTCCTC    6360

CTAATTTTTT TTTTCTCAGA ACAGTCTCAA ATCTCCAATG TTTAACCACC ATCATCCAGC    6420

AGTGGGACTT CCACCCTCGG CCCCATGCCC CCCTCCTCAT TCTTGCTTTC TTCCTCTGGG    6480

CTGACCCAGA CAGCATCATT TTGCAGTGAG GACCCCACCT ACTCCCCCAG CCCCTGGGGG    6540

CTCCATCCCC CGCCAGGTCC CTGGGGCTAC CCCCGATGGT GAGACCCCTT CAGACCCTAC    6600

AGAGACCCCA CTGCTCTCAC AGCTACAACT ACTGCCGGGA AGACGAGGAG ATCTACAAGG    6660

AGTTCTTTGA AGTAGCCAAT GATGTCATCC CCAACCTGCT GAAGGAGGCA GCCAGCTTGC    6720

TGGAGGCGGG CGAGGAGCGG CCGGGGGAGC AAAGCCAGGT GAAAGGCTGG AGCTCCAGCC    6780

TGTGTCCAGC CTCCCACCTG GACAGGGCTC CCTTCCACAG GGCCATGGGG GCTGCATGTA    6840

CGGGATTAGG GATGGCAGGA GGAAGGTGGC CCTGAGCAGA CAGCTATGTT CCCTTTTGCT    6900

ATAACTGAGG TCCTGGGCCC ACGTTGGACG GGACTGAAGG TATTTTAGAG GTTTCTACCC    6960

TGTGCCTTCA GTTTCATGGC CAGACTCCCT CCCTCAGCTG AGGGGTGGAG GTAGGGATGG    7020

TACGTCCTGG CTATGGATTG GCTTTATAAA AGGAAGAGG TTCTAAGAAT GTTCCCAACC    7080

TATGCTTACC TTTTCTGGAG CCAGGGGTCT TTGCCTAGGT GGGGGGCCTG GCCTGTGCCC    7140

TCTGCTAAGG GGTGAGTAAG AGACTGATCT GTGCCCTCCC TTCCCCCTCG TCCAGGGCAC    7200

CCAGAGCCAA GGTTCCGCCC TCCAGGACCC TGAGTGCTTC GCCCACCTGC TGCGATTCTA    7260

CGACGGCATC TGCAAATGGG AGGAGGGCAG TCCCACGCCT GTGCTGCACG TGGGCTGGGC    7320

CACCTTTCTT GTGCAGTCCC TAGGCCGTTT TGAGGGACAG GTGAGGGACA GCTGCACAGA    7380

GGTCTGGGCA CTACAGGTGG TGACAGCAGC CACGGGCTTG TCAGACTTTT CTGGCCCAGG    7440

GGCAGCATCT GCCCATCCCC TTCGGTGCCG ATGGGACTGA GACCCCCTGG GTGGGATGGG    7500

ATGGCCAGAG CAGGGTCCTG GAGTTCCAGC CACTGGCCGG CAACCTTGCT CTCACCTTGC    7560

TCTCCCCACT GGCCCAGGTG CGGCAGAAGG TGCGCATAGT GAGCCGAGAG GCCGAGGCGG    7620

CCGAGGCCGA GGAGCCGTGG GGCGAGGAAG CCCGGGAAGG CCGGCGGCGG GGCCCACGGC    7680

GGGAGTCCAA GCCAGAGGAG CCCCCGCCGC CCAAGAAGCC AGCACTGGAC AAGGGCCTGG    7740

GCACCGGCCA GGGTGCAGTG TCAGGACCCC CCCGGAAGCC TCCTGGGACT GTCGCTGGCA    7800

CAGCCCGAGG CCCTGAAGGT GGCAGACACG CTCAGGTGCC AGCACCCGCA GCATCACCAC    7860

CGCCGGAGGG TCCAGTGCTC ACTTTCCAGA GTGAGAAGAT GAAGGGCATG AAGGAGCTGC    7920

TGGTGGCCAC CAAGATCAAC TCGAGCGCCA TCAAGCTGCA ACTCACGGCA CAGTCGCAAG    7980

TGCAGATGAA GAAGCAGAAA GTGTCCACCC CTAGTGACTA CACTCTGTCT TTCCTCAAGC    8040

GGCAGCGCAA AGGCCTCTGA ACTACTGGGG ACTTCGGACC GCTTGTGGGG ACCCAGGCTC    8100

CGCCTTAGTC CCCCAACTCT GAGCCCATGT TCTGCCCCCA GCCCAAAGGG GACAGGCCTC    8160

ACCTCTACCC AAACCCTAGG TTCCCGGTCC CGAGTACAGT CTGTATCAAA CCCACGATTT    8220

TCTCCAGCTC AGAACCCAGG GCTCTGCCCC AGTCGTTAGA ATATAGGTCT CTTCTCCCAG    8280

AATCCCAGCC GGCCAATGGA AACCTCACGC TGGGTCCTAA TTACCAGTCT TTAAAGGCCC    8340

AGCCCCTAGA AACCCAAGCT CCTCCTCGGA ACCGCTCACC TAGAGCCAGA CCAACGTTAC    8400
```

```
TCAGGGCTCC TCCCAGCTTG TAGGAGCTGA GGTTTCACCC TTAACCCAAG GGAGCACAGG    8460

TCCCACCTCC AGCCCGGGGA GCCTAGGACC ACTCAGCCCC TAGGAGTATA TTTCCGCACT    8520

TCAGAATTCC ATATCTTGCG AATCCAAGCT CCCTGCCCCA AATAACTTCA GTCCTGCTTC    8580

CAGAATTTGG AAATCCTAGT TTCCTCTCCT TCGTATCCCG AGTCTGGGAC ACAAAACTCC    8640

GCCCCCAGCC TATGAGCATC CTGAGCCCCG CCCTCTTCCT GACGAAACTG GCCCCGGATC    8700

AGAGCAGGAC CTCCCTTCCG ACCCTCTGGG AACCTCCCAG AGGTCCAGCC CATCTCGGAG    8760

CATCCCGGAG GAAATCTGCA GAGGGGTTAG GAGTGGGTGA CAAGAGCCTG ATCTCTTCCT    8820

GTTTTGTACA TAGATTTATT TTTCAGTTCC AAGAAAGATG AATACATTTT GTTAAAAAAA    8880

ATATAAAGCG CAAGTCCATG TTTATCTGGG AAATTGGGGA TGGGGCGGGG AGTGGAGCGC    8940

CCCTTCTTCC CTTTGTCTTC TGGCTCCCGG GACTTTGCGC TCCCTACCTG TGGAGCGCGA    9000

GCGACAGTGG CGGCGGAAGG ACGTAGGCTC CGCCCCGGCC TTGGGGCTTC CCCCGCGCCG    9060

CCGAGGGCCC GTCCCGCGGG CGCCTCCTCC CGGACTGGCG GTGGGGCATC CCNGGGCGCG    9120

GCCCCGCCCC CGGGCTTCAG CCCCGCCCCC GCGGCTTCAG AGCCACGGGC GCCCGCCCCG    9180

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..19
        (D) OTHER INFORMATION: /note= "antisense strand from patient
            with 512delC frameshift mutation"

(xi) SEQUENCE DESCRIPTION: SEQ ID NO: 4:

GATCCTTAAG TAGGAGCGG                                                     19

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..20
        (D) OTHER INFORMATION: /note= "antisense strand from normal
            sequence (positions 500-519 of
            MEN1 cDNA"

(xi) SEQUENCE DESCRIPTION: SEQ ID NO: 5:

GATCCTTGAA GTAGGAGCGG                                                    20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(ix) FEATURE:
            (A) NAME/KEY: -
            (B) LOCATION: 1..20
            (D) OTHER INFORMATION: /note= "antisense strand from normal
                sequence (positions 1405-1424 of
                MEN1 cDNA)"

(xi) SEQUENCE DESCRIPTION: SEQ ID NO: 6:

GGTGGCCCAG CCCACGTGCA                                                      20

(2) INFORMATION FOR SEQ ID NO: 7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..20
            (D) OTHER INFORMATION: /note= "antisense strand from position
                1417 C->T substitution, resulting in
                W436X mutation"

(xi) SEQUENCE DESCRIPTION: SEQ ID NO: 7:

GGTGGCCTAG CCCACGTGCA                                                      20

(2) INFORMATION FOR SEQ ID NO: 8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

GACCTGGGTG CGCTTTCTGG AC                                                   22

(2) INFORMATION FOR SEQ ID NO: 9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

GTTGGACATA GAGGGTGTAA ACAG                                                 24

(2) INFORMATION FOR SEQ ID NO: 10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 10:

GGTGAGCTCG GGAACGTTGG TAG                                                  23

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GAGACCTTCT TCACCAGCTC ACGG                                          24

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

CGAACCTCAC AAGGCTTACA GTTC                                          24

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GTTGGACATA GAGGGTGTAA ACAG                                          24

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

ACAGTTGACA CAAAGTGAGA CTGG                                          24

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GGCTCTTCTG TCTTCCCTTC CTATG                                         25

(2) INFORMATION FOR SEQ ID NO: 16:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GGTCCCACAG CAAGTCAAGT CTGG                                             24

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

CCTGTTCCGT GGCTCATAAC TCTC                                             24

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

CCTCAGCCAG CAGTCCTGTA GA                                               22

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GGACGAGGGT GGTTGGAAAC TG                                               22

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GGACTCCTTG GGATCTTCCT GTG                                              23

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear

```
        (ii) MOLECULE TYPE: DNA (xi) SEQUENCE DESCRIPTION: SEQ ID NO: 21:

AACGACCATC ATCCAGCAGT GG                                              22

(2) INFORMATION FOR SEQ ID NO: 22:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 22:

CCATCCCTAA TCCCGTACAT GC                                              22

(2) INFORMATION FOR SEQ ID NO: 23:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 23:

TGGTGAGACC CCTTCAGACC CTAC                                            24

(2) INFORMATION FOR SEQ ID NO: 24:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 24:

CTGCTAAGGG GTGAGTAAGA GAC                                             23

(2) INFORMATION FOR SEQ ID NO: 25:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 25:

GGTTTGATAC AGACTGTACT CGG                                             23

(2) INFORMATION FOR SEQ ID NO: 26:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 26:
```

-continued

```
GTCTGACAAG CCCGTGGCTG CTG                                       23

(2) INFORMATION FOR SEQ ID NO: 27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

GCATCTGCCC ATCCCCTTCG GTG                                       23

(2) INFORMATION FOR SEQ ID NO: 28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GAAGCCTCCT GGGACTGTCG CTG                                       23
```